(12) United States Patent
Macoviak et al.

(10) Patent No.: US 11,188,873 B2
(45) Date of Patent: *Nov. 30, 2021

(54) REMOTELY-EXECUTED MEDICAL THERAPY DEVICE

(71) Applicant: WhenMed VC LLC, San Diego, CA (US)

(72) Inventors: John A. Macoviak, San Diego, CA (US); Richard L. Macoviak, Weatherly, CA (US); James J. Macoviak, Conyngham, PA (US); Espir G. Kahatt, Carlsbad, CA (US)

(73) Assignee: WhenMed VC LLC, Lewes, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/925,644

(22) Filed: Jul. 10, 2020

(65) Prior Publication Data
US 2020/0397661 A1    Dec. 24, 2020

Related U.S. Application Data

(63) Continuation of application No. 15/880,865, filed on Jan. 26, 2018, now abandoned, which is a
(Continued)

(51) Int. Cl.
*G06Q 10/10* (2012.01)
*G16H 40/67* (2018.01)
(Continued)

(52) U.S. Cl.
CPC ............ *G06Q 10/10* (2013.01); *A61J 7/0076* (2013.01); *G16H 20/13* (2018.01); *G16H 40/63* (2018.01); *G16H 40/67* (2018.01); *G16H 80/00* (2018.01)

(58) Field of Classification Search
CPC ..... G16H 20/13; G06F 19/322; G06F 19/328; G06F 19/3462; G07F 17/0092
See application file for complete search history.

(56) References Cited

U.S. PATENT DOCUMENTS 4,489,387 A   12/1984   Lamb et al.
4,491,725 A    1/1985   Pritchard
(Continued)

FOREIGN PATENT DOCUMENTS

WO    WO-2013077977 A1    5/2013
WO    WO-2014130880 A1    8/2014

OTHER PUBLICATIONS

Notice of Allowance dated Oct. 25, 2017 for U.S. Appl. No. 14/253,450.
(Continued)

*Primary Examiner* — Timothy R Waggoner
(74) *Attorney, Agent, or Firm* — Blank Rome LLP

(57) ABSTRACT

Devices, systems, and software for providing remote medical therapy to a subject comprising: an apparatus for dispensing one or more medical items from an inventory of medical items, the inventory of medical items risk profiled to a subject, a population, a venue, or a situation; and a connector device comprising: at least one means for communicating with the apparatus for dispensing one or more medical items from an inventory of medical items; at least one means for communicating with a technology device; and a software module enabling communications between the apparatus for dispensing one or more medical items from an inventory of medical items and the technology device.

14 Claims, 12 Drawing Sheets

Related U.S. Application Data continuation of application No. 14/253,450, filed on Apr. 15, 2014, now Pat. No. 9,907,730, which is a continuation of application No. 14/017,188, filed on Sep. 3, 2013, now Pat. No. 8,751,039.

(60) Provisional application No. 61/826,348, filed on May 22, 2013, provisional application No. 61/810,269, filed on Apr. 10, 2013, provisional application No. 61/767,956, filed on Feb. 22, 2013.

(51) Int. Cl.
*A61J 7/00* (2006.01)
*G16H 20/13* (2018.01)
*G16H 80/00* (2018.01)
*G16H 40/63* (2018.01)

(56) References Cited

U.S. PATENT DOCUMENTS

| | | | |
|---|---|---|---|
| 4,731,725 A | 3/1988 | Suto et al. | |
| 4,847,764 A | 7/1989 | Halvorson et al. | |
| 4,945,476 A | 7/1990 | Bodick et al. | |
| 4,975,840 A | 12/1990 | DeTore et al. | |
| 5,084,828 A | 1/1992 | Kaufman | |
| 5,099,424 A | 3/1992 | Schneiderman | |
| 5,130,936 A | 7/1992 | Sheppard et al. | |
| 5,235,510 A | 8/1993 | Yamada et al. | |
| 5,404,292 A | 4/1995 | Hendrickson | |
| 5,410,471 A | 4/1995 | Alyfuku et al. | |
| 5,437,278 A | 8/1995 | Wilk | |
| 5,492,117 A | 2/1996 | Eisenberg et al. | |
| 5,517,405 A | 5/1996 | McAndrew et al. | |
| 5,594,637 A | 1/1997 | Eisenberg et al. | |
| 5,657,236 A | 8/1997 | Conkright | |
| 5,692,501 A | 12/1997 | Minturn | |
| 5,713,485 A | 2/1998 | Liff et al. | |
| 5,746,204 A | 5/1998 | Schauss | |
| 5,764,923 A | 6/1998 | Tallman et al. | |
| 5,796,759 A | 8/1998 | Eisenberg et al. | |
| 5,807,256 A | 9/1998 | Taguchi et al. | |
| 5,867,821 A | 2/1999 | Ballantyne et al. | |
| 5,956,689 A | 9/1999 | Everhart, III | |
| 5,993,386 A | 11/1999 | Ericsson | |
| 6,004,020 A | 12/1999 | Bartur | |
| 6,059,724 A | 5/2000 | Campell et al. | |
| 6,063,026 A | 5/2000 | Schauss et al. | |
| 6,068,156 A | 5/2000 | Liff et al. | |
| 6,101,478 A | 8/2000 | Brown | |
| 6,206,829 B1 | 3/2001 | Iliff | |
| 6,219,587 B1 | 4/2001 | Ahlin et al. | |
| 6,234,964 B1 | 5/2001 | Iliff | |
| 6,322,504 B1 | 11/2001 | Kirshner | |
| 6,334,192 B1 | 12/2001 | Karpf | |
| 6,352,200 B1 | 3/2002 | Schoonen et al. | |
| 6,602,469 B1 | 8/2003 | Maus et al. | |
| 6,752,787 B1 | 6/2004 | Causey, III et al. | |
| 6,757,898 B1 | 6/2004 | Ilsen et al. | |
| 7,048,141 B2 | 5/2006 | Abdulhay et al. | |
| 7,072,738 B2 | 7/2006 | Bonney | |
| 7,306,562 B1 | 12/2007 | Baykal | |
| 7,379,885 B1 | 5/2008 | Zakim | |
| 7,395,216 B2 | 7/2008 | Rosenfeld et al. | |
| RE40,453 E | 8/2008 | Lasher et al. | |
| RE40,510 E | 9/2008 | Lasher et al. | |
| 7,447,643 B1 | 11/2008 | Olson et al. | |
| 7,483,766 B1 | 1/2009 | Frankel | |
| 7,590,550 B2 | 9/2009 | Schoenberg | |
| 7,739,126 B1 | 6/2010 | Cave et al. | |
| 7,801,745 B2 | 9/2010 | Walker et al. | |
| 7,853,355 B1 | 12/2010 | Willemse et al. | |
| 7,912,582 B1 | 3/2011 | Holtje et al. | |
| 7,996,106 B2 | 8/2011 | Ervin | |
| RE42,730 E | 9/2011 | Lasher et al. | |
| 8,014,170 B2 | 9/2011 | Mori et al. | |
| 8,391,104 B2 | 3/2013 | de la Huerga | |
| 8,666,539 B2 | 3/2014 | Ervin | |
| 8,751,039 B1 * | 6/2014 | Macoviak | G16H 80/00 700/244 |
| 8,922,367 B2 | 12/2014 | Denny et al. | |
| 9,202,253 B2 | 12/2015 | Macoviak et al. | |
| 9,224,180 B2 | 12/2015 | Macoviak et al. | |
| 9,907,730 B2 | 3/2018 | Macoviak | |
| 2002/0004725 A1 | 1/2002 | Martin et al. | |
| 2002/0029157 A1 | 3/2002 | Marchosky | |
| 2002/0070226 A1 | 6/2002 | Liff et al. | |
| 2002/0077865 A1 | 6/2002 | Sullivan | |
| 2002/0087276 A1 | 7/2002 | Otvos | |
| 2002/0133379 A1 | 9/2002 | Lewis et al. | |
| 2002/0169637 A1 | 11/2002 | Akers et al. | |
| 2002/0198738 A1 | 12/2002 | Osborne | |
| 2003/0055531 A1 | 3/2003 | Liff et al. | |
| 2003/0065241 A1 | 4/2003 | Hohnloser | |
| 2003/0074218 A1 | 4/2003 | Liff et al. | |
| 2003/0105731 A1 | 6/2003 | Lapointe et al. | |
| 2003/0189058 A1 | 10/2003 | Liff et al. | |
| 2003/0191671 A1 | 10/2003 | Ulrich et al. | |
| 2003/0216831 A1 | 11/2003 | Hart et al. | |
| 2004/0037738 A1 | 2/2004 | Maus et al. | |
| 2004/0065053 A1 | 4/2004 | Rice et al. | |
| 2004/0088187 A1 | 5/2004 | Chudy et al. | |
| 2004/0133452 A1 | 7/2004 | Denny et al. | |
| 2004/0164146 A1 | 8/2004 | Rosenblum | |
| 2004/0210548 A1 | 10/2004 | Ketcherside et al. | |
| 2004/0215369 A1 | 10/2004 | Rosenblum | |
| 2005/0010088 A1 | 1/2005 | Iliff | |
| 2005/0010444 A1 | 1/2005 | Iliff | |
| 2005/0071200 A1 | 3/2005 | Franklin et al. | |
| 2005/0080462 A1 | 4/2005 | Jenkins et al. | |
| 2005/0113969 A1 | 5/2005 | Spano, Jr. et al. | |
| 2005/0171512 A1 | 8/2005 | Flaherty | |
| 2006/0173708 A1 | 8/2006 | Vining et al. | |
| 2006/0224416 A1 | 10/2006 | Lloyd et al. | |
| 2006/0265253 A1 | 11/2006 | Rao et al. | |
| 2007/0084150 A1 | 4/2007 | Siegel et al. | |
| 2007/0093934 A1 | 4/2007 | Garneau, III | |
| 2007/0094048 A1 | 4/2007 | Grichnik | |
| 2007/0118399 A1 | 5/2007 | Avinash et al. | |
| 2007/0119930 A1 | 5/2007 | Jordan et al. | |
| 2007/0168308 A1 | 7/2007 | Wang et al. | |
| 2007/0179769 A1 | 8/2007 | Grichnik et al. | |
| 2007/0293982 A1 | 12/2007 | Rosenblum | |
| 2008/0015894 A1 | 1/2008 | Miller et al. | |
| 2008/0033761 A1 | 2/2008 | Brummel et al. | |
| 2008/0097943 A1 | 4/2008 | Kelly et al. | |
| 2008/0099684 A1 | 5/2008 | Murakami et al. | |
| 2008/0162352 A1 | 7/2008 | Gizewski | |
| 2008/0179387 A1 | 7/2008 | Cantlay et al. | |
| 2008/0288105 A1 | 11/2008 | Mauger et al. | |
| 2009/0048712 A1 | 2/2009 | Rosenblum | |
| 2009/0069746 A1 | 3/2009 | Miller et al. | |
| 2009/0240528 A1 | 9/2009 | Bluth | |
| 2009/0295575 A1 | 12/2009 | Kennedy | |
| 2009/0315702 A1 | 12/2009 | Cohen et al. | |
| 2010/0205009 A1 | 8/2010 | Kostoff | |
| 2010/0268190 A1 | 10/2010 | Mielenz | |
| 2010/0268377 A1 | 10/2010 | Pinney et al. | |
| 2010/0274573 A1 | 10/2010 | Feied et al. | |
| 2010/0324728 A1 | 12/2010 | Rosenblum | |
| 2010/0324936 A1 | 12/2010 | Vishnubhatla et al. | |
| 2011/0009824 A1 | 1/2011 | Yodfat et al. | |
| 2011/0092825 A1 | 4/2011 | Gopinathan et al. | |
| 2014/0058755 A1 | 2/2014 | Macoviak et al. | |
| 2016/0055307 A1 | 2/2016 | Macoviak et al. | |

OTHER PUBLICATIONS

Office Action dated Oct. 12, 2016 for U.S. Appl. No. 14/253,450.
Office Action dated Feb. 19, 2016 for U.S. Appl. No. 14/253,450.
U.S. Appl. No. 14/253,450 Office Action dated Feb. 19, 2016.
U.S. Appl. No. 14/253,450 Office Action dated Oct. 12, 2016.
Alonzo et al. Distribution Free ROC Analysis Using Binary Regression Technique. Biostatistics 3(3):421-432 (2002).

(56) References Cited

OTHER PUBLICATIONS

Apache II calculator (available at www.globalrph.com/apacheii.htm) downloaded Apr. 22, 2011.
Breiman. Random Forests. Machine Learning 45:5-32 (2001).
Decision Support Systems (available at www.openclinical.org/dss.html) downloaded Apr. 22, 2011.
Dxplain (available at http://lcs.mgh.harvard.edu/projects/dxplain.html).
Goldman et al. A Computer Protocol to Predict Myocardial Infarction in Emergency Department Patients with Chest Pain. New England Journal of Medicine 318:797-803 (1998).
Hales et al. Factors Impacting the Success of Computerized Preadmission Screening. Proceedings of the Annual Symposium on Computer Applications in Medical Care pp. 728-732 (1995).
Hales et al. Integration of a Stand Alone Expert System with a Hospital Information System. Proceedings of the Annual Symposium on Computer Applications in Medical Care pp. 427-432 (1992).
Hall et al. An Electronic Application for Rapidly Calculating Charlson Comorbidity Score. BMC Cancer 4:94-101 (2004).
Mair et al. A Decision Tree for the Early Diagnosis of Acute Myocardial Infarction in Nontraumatic Chest Pain Patients at Hospital Admission. Chest 108(6):1502-1509 (1995).
Miller et al. Internist-1: An Experimental Computer-Based Diagnostic Consultant for General Internal Medicine. New England Journal of Medicine 307(8):468-476 (1982).
Olsson. Charlson Comorbidity Index Can Add Prognostic Information to Rapid Emergency Medicine Score as a Predictor of Long-Term Mortality. European Journal of Emergency Medicine 12(5):220-224 (2005).
Olsson. Comparison of the Rapid Emergency Medicine Score and Apache II in Nonsurgical Emergency Department Patients. Academic Emergency Medicine 10(10):1040-1048 (2003).
Olsson et al. Rapid Emergency Medicine Score: A New Prognostic Tool for In-hospital Mortality in Nonsurgical Emergency Department Patients. Journal of Internal Medicine 255:579-587 (2004).
PCT/US2012/020390 International Search Report dated Jul. 30, 2012.
PCT/US2012/062865 International Preliminary Report on Patentability dated Jun. 5, 2014.
PCT/US2012/062865 International Search Report and Written Opinion dated Mar. 15, 2013.
PCT/US2014/017811 International Search Report and Written Opinion dated Jun. 12, 2014.
Rapid Acute Physiology Score 1.0 (available at http://handheld.softpedia.com/get/Educational/Medical/Rapid-Acute-Physiology-Score-16722.shtml).
Rhee et al. Rapid Acute Physiology Scoring in Transport Systems. Critical Care Medicine 18(10):1119-1123 (1990).
Rhee et al. The Rapid Acute Physiology Score. The American Journal of Emergency Medicine 5(4):278-282 (Jul. 1987).
Shortliffe et al. A Model of Inexact Reasoning in Medicine. Mathematical Biosciences 23:351-379 (1975).
Stineman et al. Classifying Rehabilitation Inpatients by Expected Functional Gain. Medical Care 35(9):963-973 (1997).
U.S. Appl. No. 61/732,753, filed Dec. 3, 2012.
U.S. Appl. No. 12/986,027 Office Action dated Oct. 3, 2012.
U.S. Appl. No. 14/017,188 Office Action dated Nov. 7, 2013.
U.S. Appl. No. 14/092,783 Office Action dated Apr. 14, 2014.
U.S. Appl. No. 14/092,783 Office Action dated Jan. 27, 2014.
U.S. Appl. No. 14/092,783 Office Action dated Nov. 17, 2014.
U.S. Appl. No. 14/595,094 Office Action dated Mar. 4, 2015.
Zhang et al. Model Selection via Multifold Cross Validation. The Annals of Statistics 21(1):299-313 (1993).

* cited by examiner

REMOTELY-EXECUTED MEDICAL THERAPY DEVICE

CROSS-REFERENCE TO RELATED APPLICATIONS

This application is a continuation of and which claims the benefit of the filing date and disclosure of U.S. patent application Ser. No. 15/880,865, filed on Jan. 26, 2018, entitled "Remotely-Executed Medical Therapy Device," which is a continuation of and claims the benefit of the filing date of U.S. patent application Ser. No. 14/253,450, now U.S. Pat. No. 9,907,730, filed Apr. 15, 2014, which is a continuation of and claims the benefit of the filing date of U.S. patent application Ser. No. 14/017,188, now U.S. Pat. No. 8,751,039, filed on Sep. 3, 2013, which is based on and claims the benefit of the filing dates of U.S. Provisional Patent Application No. 61/767,956, filed Feb. 22, 2013, U.S. Provisional Patent Application No. 61/810,269, filed Apr. 10, 2013, and U.S. Provisional Patent Application No. 61/826,348, filed May 22, 2013, the contents of each of which are incorporated by reference herein.

BACKGROUND OF THE INVENTION

A wide variety of circumstances result in inadequate access to healthcare for many individuals and families. Some lack adequate access because they live in isolated, rural, or other governmentally designated underserved areas. Some lack adequate access because they are uninsured or underinsured. Others live in developing countries where medical training and infrastructure is yet to be developed. Circumstances render some individuals without adequate access to healthcare in natural and manmade disaster areas and battlefields.

Moreover, the cost of providing adequate healthcare is rising. While more money is spent on health care per person in the U.S. than in any other nation in the world, in 2009, the U.S. Census Bureau reported that 16.7% of the population was uninsured. Current estimates put U.S. health care spending at approximately 16% of GDP. Growth in healthcare spending is projected to average 6.7% annually over the period 2007 through 2017. High healthcare costs also affect individuals. A 2007 study found that 62.1% of filers for bankruptcy cited high medical expenses as a contributing factor.

BRIEF SUMMARY OF THE INVENTION

In one aspect, disclosed herein are devices for providing remote medical therapy to a subject in a healthcare encounter, the device comprising a processor and a memory device, the device further comprising: a housing; at least one means for communicating with an apparatus for dispensing one or more medical items from an inventory of medical items, the inventory of medical items risk profiled to a subject, a population, a venue, an event, or a situation; at least one means for communicating with a technology device; and a software module enabling communications between the apparatus for dispensing one or more medical items from an inventory of medical items and the technology device. In some embodiments, the device further comprises a magnetic stripe reader. In further embodiments, the magnetic stripe reader is adapted to read data on a magnetic stripe associated with an insurance card, financial transaction card, membership card, or the apparatus for dispensing one or more medical items from an inventory of medical items. In further embodiments, the at least one means for communicating with an apparatus for dispensing one or more medical items from an inventory of medical items is a magnetic stripe reader. In some embodiments, the at least one means for communicating with an apparatus for dispensing one or more medical items from an inventory of medical items is a connector selected from: data port, audio jack, microphone jack, Ethernet, FireWire, mini-USB, micro-USB, USB Type A, and USB Type B. In further embodiments, the connector is reversibly retractable within the housing. In further embodiments, the connector swivels about an axis with respect to the housing. In some embodiments, the at least one means for communicating with an apparatus for dispensing one or more medical items from an inventory of medical items is a wireless interface selected from: Bluetooth, ZigBee, Wi-Fi, near field communication, radio-frequency identification, and infrared. In some embodiments, the device further comprises a confirmation component, the confirmation component indicating if a correct apparatus for dispensing one or more medical items is in communication with the device. In further embodiments, the confirmation component provides visual confirmation, audible confirmation, tactile confirmation, or a combination thereof. In some embodiments, the technology device is a computer, a mobile device, a hard wired telephone, a set top box, an internet appliance, or medical diagnostic device. In some embodiments, the technology device is a networked device including a software module for securely accessing one or more electronic health records for the subject. In some embodiments, the at least one means for communicating with a technology device is a connector selected from: data port, audio jack, microphone jack, Ethernet, FireWire, mini-USB, micro-USB, USB Type A, and USB Type B. In further embodiments, the connector is reversibly retractable within the housing. In further embodiments, the connector swivels about an axis with respect to the housing. In some embodiments, the at least one means for communicating with a technology device is a wireless interface selected from: Bluetooth, ZigBee, Wi-Fi, near field communication, radio-frequency identification, and infrared. In some embodiments, the device further comprises a software module for remote monitoring or operation of the device by a telemedical care provider. In further embodiments, the telemedical care provider is selected from the group consisting of: a physician, a pharmacist, a dentist, a physician assistant, a nurse practitioner, a registered nurse, a pharmacist, a chiropractor, an emergency medical technician, a licensed practical nurse, a certified ultrasound technician, a psychologist, a social worker, a military medic, a physical therapist, an occupational therapist, a speech therapist, a radiology technician, a cardiac catheterization technician, a clinical pathology laboratory technician, a medical aesthetician, a licensed medical technologist, a toxicologist consultant, a credentialed medical legal consultant, a credentialed hospital operations administrator, veterinarian or a veterinary nurse, assistant, or technician. In further embodiments, the telemedical care provider is the subject's primary care physician. In further embodiments, the subject's primary care physician selects at least one adjunct healthcare provider identified or selected based on one or more of: type of patient's condition, severity of patient's condition, patient's insurance eligibility, and availability of one or more adjunct healthcare providers. In still further embodiments, the at least one adjunct healthcare provider is credentialed by the subject's primary care provider to provide: remote diagnosis and therapy, telemedical services, urgent care services, outpatient services, acute care services, pharmacy services, insurance services to the subject, or a combination thereof. In some embodiments, the device further comprises a software module enabling the selection of at least one adjunct healthcare provider from a database of healthcare providers to be credentialed by the subject's primary care physician for providing: remote diagnosis and therapy, telemedical services, urgent care services, outpatient services, acute care services, pharmacy services, insurance services to the subject, or a combination thereof. In some embodiments, the device further comprises a software module for identifying a subject. In some embodiments, the device further comprises a biosensor. In further embodiments, the biosensor is adapted to collect medical information from a subject or the subject's environment. In some embodiments, the inventory of medical items is determined by profiling health or economic risk for a subject, a population, a venue, an event, or a situation in advance of need for the medical items. In further embodiments, the inventory of medical items is risk profiled by determining a statistical level of likelihood that the items will be needed within 2 years, within 1 year, within 6 months, within 1 month, within 2 weeks, within 1 week, or within 1 day. In further embodiments, risk profiling analysis comprises performing statistical analysis, performing probability calculations, making recommendations, and making outcome predictions to predict a health or economic outcome of a patient or therapy, wherein said prediction is real-time, individualized, and probabilistic-based and uses historic, peer-reviewed health or economic data and emerging health or economic data. In some embodiments, the inventory of medical items comprises items that require a prescription from a licensed healthcare provider. In further embodiments, the inventory of medical items comprises: one or more medications, one or more therapeutic devices, one or more diagnostic devices, or one or more diagnostic kits.

In another aspect, disclosed herein are systems for providing remote medical therapy to a subject in a healthcare encounter, the system comprising: an apparatus for dispensing one or more medical items from an inventory of medical items, the inventory of medical items risk profiled to a subject, a population, a venue, or a situation; and a connector device comprising: a processor; a memory; at least one means for communicating with the apparatus for dispensing one or more medical items from an inventory of medical items; at least one means for communicating with a technology device; and a software module enabling communications between the apparatus for dispensing one or more medical items from an inventory of medical items and the technology device. In some embodiments, the apparatus for dispensing one or more medical items from an inventory of medical items comprises a magnetic stripe reader. In further embodiments, the magnetic stripe reader reads data on a magnetic stripe associated with an insurance card, financial transaction card, membership card, or the connector device. In some embodiments, the connector device or the technology device comprises a software module for providing instantaneous encounter-specific financial insurance coverage, wherein said insurance includes a level of guarantee and an associated premium. In further embodiments, the connector device or the technology device comprises a software module for processing payment. In some embodiments, the apparatus for dispensing one or more medical items from an inventory of medical items comprises one or more tamper-proof or child-proof elements. In further embodiments, the apparatus for dispensing one or more medical items from an inventory of medical items comprises a removable, opaque sleeve. In further embodiments, the apparatus for dispensing one or more medical items from an inventory of medical items comprises a tamper-proof or child-proof opening mechanism. In further embodiments, the apparatus for dispensing one or more medical items from an inventory of medical items comprises a tamper-proof or child-proof protective wrapper. In some embodiments, the connector device comprises a magnetic stripe reader. In further embodiments, the magnetic stripe reader is adapted to read data on a magnetic stripe associated with an insurance card, financial transaction card, membership card, or the apparatus for dispensing one or more medical items from an inventory of medical items. In some embodiments, the at least one means for communicating with an apparatus for dispensing one or more medical items from an inventory of medical items is a magnetic stripe reader. In some embodiments, the at least one means for communicating with an apparatus for dispensing one or more medical items from an inventory of medical items is a connector selected from: data port, audio jack, microphone jack, Ethernet, FireWire, mini-USB, micro-USB, USB Type A, and USB Type B. In further embodiments, the connector is reversibly retractable within the housing. In further embodiments, the connector swivels about an axis with respect to the housing. In some embodiments, the at least one means for communicating with an apparatus for dispensing one or more medical items from an inventory of medical items is a wireless interface selected from: Bluetooth, ZigBee, Wi-Fi, near field communication, radio-frequency identification, and infrared. In some embodiments, the connector device further comprises a confirmation component, the confirmation component indicating if a correct apparatus for dispensing one or more medical items is in communication with the device. In further embodiments, the confirmation component provides visual confirmation, audible confirmation, tactile confirmation, or a combination thereof. In some embodiments, the technology device is a computer, a mobile device, a hard wired telephone, a set top box, an internet appliance, or a medical diagnostic device. In some embodiments, the technology device is a networked device including a software module for securely accessing one or more electronic health records for the subject. In some embodiments, the at least one means for communicating with a technology device is a connector selected from: data port, audio jack, microphone jack, Ethernet, FireWire, mini-USB, micro-USB, USB Type A, and USB Type B. In further embodiments, the connector is reversibly retractable within the housing. In further embodiments, the connector swivels about an axis with respect to the housing. In some embodiments, the at least one means for communicating with a technology device is a wireless interface selected from: Bluetooth, ZigBee, Wi-Fi, near field communication, radio-frequency identification, and infrared. In some embodiments, the connector device or the technology device comprises a software module for remote monitoring or operation of the device by a telemedical care provider. In further embodiments, the telemedical care provider is selected from the group consisting of: a physician, a pharmacist, a dentist, a physician assistant, a nurse practitioner, a registered nurse, a pharmacist, a chiropractor, an emergency medical technician, a licensed practical nurse, a certified ultrasound technician, a psychologist, a social worker, a military medic, a physical therapist, an occupational therapist, a speech therapist, a radiology technician, a cardiac catheterization technician, a clinical pathology laboratory technician, a medical aesthetician, a licensed medical technologist, a toxicologist consultant, a credentialed medical legal consultant, a credentialed hospital operations administrator, veterinarian or a veterinary nurse, assistant, or technician. In further embodiments, the telemedical care provider is the subject's primary care physician. In still further embodiments, the subject's primary care physician selects at least one adjunct healthcare provider identified or selected based on one or more of: type of patient's condition, severity of patient's condition, patient's insurance eligibility, and availability of one or more adjunct healthcare providers. In still further embodiments, the at least one adjunct healthcare provider is credentialed by the subject's primary care provider to provide: remote diagnosis and therapy, telemedical services, urgent care services, outpatient services, acute care services, pharmacy services, insurance services to the subject, or a combination thereof. In some embodiments, the connector device or the technology device further comprises a software module enabling the selection of at least one adjunct healthcare provider from a database of healthcare providers to be credentialed by the subject's primary care physician for providing: remote diagnosis and therapy, telemedical services, urgent care services, outpatient services, acute care services, pharmacy services, insurance services to the subject, or a combination thereof. In some embodiments, the connector device or the technology device comprises software module for identifying a subject. In some embodiments, the connector device or the technology device comprises a biosensor. In further embodiments, the biosensor is adapted to collect medical information from a subject or the subject's environment. In some embodiments, the inventory of medical items is determined by profiling health or economic risk for a subject, a population, a venue, an event, or a situation in advance of need for the medical items. In further embodiments, the inventory of medical items is risk profiled by determining a statistical level of likelihood that the items will be needed within 2 years, within 1 year, within 6 months, within 1 month, within 2 weeks, within 1 week, or within 1 day. In further embodiments, risk profiling analysis comprises performing statistical analysis, performing probability calculations, making recommendations, and making outcome predictions to predict a health or economic outcome of a patient or therapy, wherein said prediction is real-time, individualized, and probabilistic-based and uses historic, peer-reviewed health or economic data and emerging health or economic data. In some embodiments, the inventory of medical items comprises items that require a prescription from a licensed healthcare provider. In further embodiments, the inventory of medical items comprises: one or more medications, one or more therapeutic devices, one or more diagnostic devices, or one or more diagnostic kits.

In another aspect, disclosed herein are devices for providing remote medical therapy to a subject in a healthcare encounter, the device comprising a processor and a memory device, the device further comprising: a housing; a communications connection for communicating with an apparatus for dispensing one or more medical items from an inventory of medical items, the inventory of medical items risk profiled to a subject, a population, a venue, an event, or a situation; a communications connection for communicating with a technology device, the technology device comprising a software module for remote monitoring or operation of the device by a telemedical care provider; a software module enabling communications between a connected apparatus for dispensing one or more medical items from an inventory of medical items and a connected technology device; and a confirmation component, the confirmation component indicating if the correct apparatus for dispensing one or more medical items is in communication with the device. In some embodiments, the device further comprises a magnetic stripe reader, the magnetic stripe reader within a slot of the housing. In further embodiments, the magnetic stripe reader is adapted to read data on a magnetic stripe associated with an insurance card, financial transaction card, membership card, or the apparatus for dispensing one or more medical items from an inventory of medical items. In some embodiments, the communications connection for communicating with an apparatus for dispensing one or more medical items from an inventory of medical items is a magnetic stripe reader. In some embodiments, the communications connection for communicating with an apparatus for dispensing one or more medical items from an inventory of medical items is a connector selected from: data port, audio jack, microphone jack, Ethernet, FireWire, mini-USB, micro-USB, USB Type A, and USB Type B. In further embodiments, the connector is reversibly retractable within the housing. In further embodiments, the connector swivels about an axis with respect to the housing. In some embodiments, the communications connection for communicating with an apparatus for dispensing one or more medical items from an inventory of medical items is a wireless interface selected from: Bluetooth, ZigBee, Wi-Fi, near field communication, radio-frequency identification, and infrared. In some embodiments, the confirmation component provides visual confirmation, audible confirmation, tactile confirmation, or a combination thereof. In some embodiments, the technology device is a computer, a mobile device, a hard wired telephone, a set top box, or medical diagnostic device. In some embodiments, the technology device is a networked device including a software module for securely accessing one or more electronic health records for the subject. In some embodiments, the communications connection for communicating with a technology device is a connector selected from: data port, audio jack, microphone jack, Ethernet, FireWire, mini-USB, micro-USB, USB Type A, and USB Type B. In further embodiments, the connector is reversibly retractable within the housing. In further embodiments, the connector swivels about an axis with respect to the housing. In some embodiments, the communications connection for communicating with an apparatus for dispensing one or more medical items from an inventory of medical items is a wireless interface selected from: Bluetooth, ZigBee, Wi-Fi, near field communication, radio-frequency identification, and infrared. In some embodiments, the telemedical care provider is selected from the group consisting of: a physician, a pharmacist, a dentist, a physician assistant, a nurse practitioner, a registered nurse, a pharmacist, a chiropractor, an emergency medical technician, a licensed practical nurse, a certified ultrasound technician, a psychologist, a social worker, a military medic, a physical therapist, an occupational therapist, a speech therapist, a radiology technician, a cardiac catheterization technician, a clinical pathology laboratory technician, a medical aesthetician, a licensed medical technologist, a toxicologist consultant, a credentialed medical legal consultant, a credentialed hospital operations administrator, veterinarian or a veterinary nurse, assistant, or technician. In some embodiments, the telemedical care provider is the subject's primary care physician. In further embodiments, the subject's primary care physician selects at least one adjunct healthcare provider identified or selected based on one or more of: type of patient's condition, severity of patient's condition, patient's insurance eligibility, and availability of one or more adjunct healthcare providers. In still further embodiments, the at least one adjunct healthcare provider is credentialed by the subject's primary care provider to provide: remote diagnosis and therapy, telemedical services, urgent care services, outpatient services, acute care services, pharmacy services, insurance services to the subject, or a combination thereof. In some embodiments, the device further comprises a software module enabling the selection of at least one adjunct healthcare provider from a database of healthcare providers to be credentialed by the subject's primary care physician for providing: remote diagnosis and therapy, telemedical services, urgent care services, outpatient services, acute care services, pharmacy services, insurance services to the subject, or a combination thereof. In some embodiments, the device further comprises software module for identifying a subject. In some embodiments, the device further comprises a biosensor. In further embodiments, the biosensor is adapted to collect medical information from a subject or the subject's environment. In some embodiments, the inventory of medical items is determined by profiling health or economic risk for a subject, a population, a venue, an event, or a situation in advance of need for the medical items. In further embodiments, the inventory of medical items is risk profiled by determining a statistical level of likelihood that the items will be needed within 2 years, within 1 year, within 6 months, within 1 month, within 2 weeks, within 1 week, or within 1 day. In further embodiments, risk profiling analysis comprises performing statistical analysis, performing probability calculations, making recommendations, and making outcome predictions to predict a health or economic outcome of a patient or therapy, wherein said prediction is real-time, individualized, and probabilistic-based and uses historic, peer-reviewed health or economic data and emerging health or economic data. In some embodiments, the inventory of medical items comprises items that require a prescription from a licensed healthcare provider. In further embodiments, the inventory of medical items comprises: one or more medications, one or more therapeutic devices, one or more diagnostic devices, or one or more diagnostic kits. In some embodiments, the device further comprises a software module for providing instantaneous encounter-specific financial insurance coverage, wherein said insurance includes a level of guarantee and an associated premium. In further embodiments, the device further comprises a software module for processing payment.

DETAILED DESCRIPTION OF THE INVENTION

Figure 1:
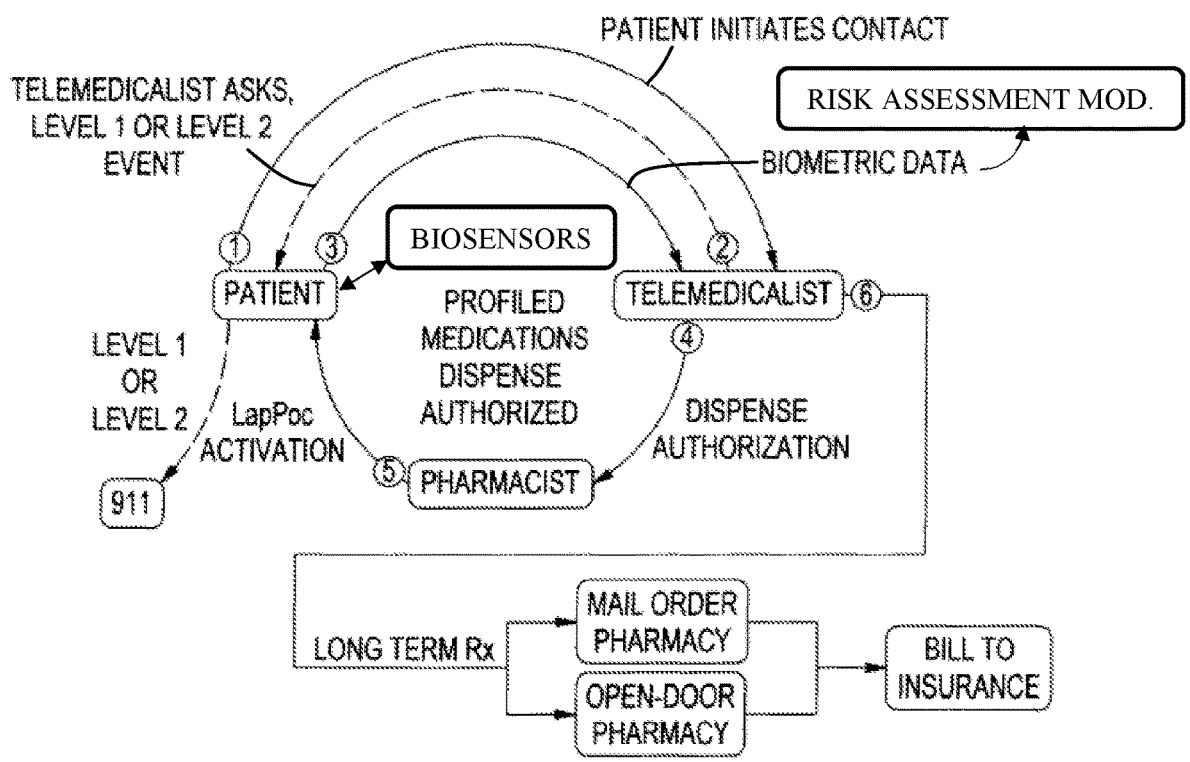
FIG. 1 shows a non-limiting example of an overall process flow for providing remote diagnosis and therapy to a subject; in this case, a process flow including interaction between a patient and a telemedical care provider, collection of patient biometric data, and remote dispensing of a short-term supply of a prescribed medication authorized by a pharmacist, followed by issuance of a long-term prescription and subsequent billing.

Described herein, in certain embodiments, are devices for providing remote medical therapy to a subject in a healthcare encounter, the device comprising a processor and a memory device, the device further comprising: a housing; at least one means for communicating with an apparatus for dispensing one or more medical items from an inventory of medical items, the inventory of medical items risk profiled to a subject, a population, a venue, an event, or a situation; at least one means for communicating with a technology device; and a software module enabling communications between the apparatus for dispensing one or more medical items from an inventory of medical items and the technology device.

Also described herein, in certain embodiments, are systems for providing remote medical therapy to a subject in a healthcare encounter, the systems comprising: an apparatus for dispensing one or more medical items from an inventory of medical items, the inventory of medical items risk profiled to a subject, a population, a venue, or a situation; and a connector device comprising: a processor; a memory; at least one means for communicating with the apparatus for dispensing one or more medical items from an inventory of medical items; at least one means for communicating with a technology device; and a software module enabling communications between the apparatus for dispensing one or more medical items from an inventory of medical items and the technology device.

Also described herein, in certain embodiments, are devices for providing remote medical therapy to a subject in a healthcare encounter, the device comprising a processor and a memory device, the device further comprising: a housing; a communications connection for communicating with an apparatus for dispensing one or more medical items from an inventory of medical items, the inventory of medical items risk profiled to a subject, a population, a venue, an event, or a situation; a communications connection for communicating with a technology device, the technology device comprising a software module for remote monitoring or operation of the device by a telemedical care provider; a software module enabling communications between a connected apparatus for dispensing one or more medical items from an inventory of medical items and a connected technology device; and a confirmation component, the confirmation component indicating if the correct apparatus for dispensing one or more medical items is in communication with the device.

Certain Definitions

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

In some embodiments, as used herein, "subject" refers to a human being requesting or in need of healthcare, healthcare-related goods and/or services or health related insurance or financial products and/or services. In some cases, a subject is a patient. In further cases, a subject interacts with the devices and systems described herein. In other cases, a subject is represented, for example, by a friend, relative, caregiver, healthcare provider, first responder, etc. and the representative interacts with the systems and devices described herein. In other embodiments, as used herein, "subject" refers to a non-human animal in need of healthcare. In further cases, a subject is a veterinary patient and an owner, rescuer, or veterinary healthcare provider interacts with the systems and devices described herein.

In some embodiments, as used herein, "onsite patient caregiver" refers to a person who has an interest in, or responsibility for, the health and welfare of a patient and is present with the patient at least once, intermittently, often, or full-time. Non-limiting examples of onsite patient caregivers include employees of a patient, members of a patient's family, hospice workers, and emergency medical technicians, paramedics, police officers, and firefighters.

In some embodiments, as used herein, "outpatient" refers to a subject or a situation not requiring or warranting overnight hospitalization.

In some embodiments, as used herein, "acute care" refers to short-term treatment for an urgent medical condition such as a severe injury or episode of illness.

In some embodiments, as used herein, "urgent care" refers to delivery of outpatient care outside of a hospital emergency department, usually on an unscheduled, walk-in basis.

In some embodiments, as used herein, "telemedicology" refers to a branch of medicine or surgery requiring specialized, formal, peer-reviewed training as a specialty or sub-specialty of medicine concerned with safely and efficaciously providing remote diagnosis and therapy via telemedicine technology and equipment.

In some embodiments, as used herein, "telemedicologist" refers to a physician, surgeon, dentist, and/or veterinarian, specialized in telemedicology and providing remote diagnosis and therapy via telemedicine technology and equipment.

In some embodiments, as used herein, "telemedical care provider" or "TCP" refers to a healthcare worker trained and engaged in provision of remote diagnosis and therapy via telemedicine technology and equipment. The term, as used herein, includes telemedicologists as well as licensed physician extenders directly supervised by or reporting to a telemedicologist in activity related to the provision of remote diagnosis and therapy via telemedicine technology and equipment. In some cases, physician extenders directly supervised by or reporting to a telemedicologist include, nurse practitioners, physician assistants, registered nurses, licensed vocational nurses, emergency medical technicians, and the like.

In some embodiments, as used herein, "telemedicalist" refers to a physician specialized in the delivery of telemedical care to acutely ill hospitalized subjects.

In some embodiments, as used herein, "health program" refers to any legal, organizational, or financial arrangement for providing healthcare services and/or healthcare administration to subjects. In various embodiments, a health program includes, by way of non-limiting examples, a healthcare maintenance membership program, a HMO, a PPO, an IPA, a pre-paid health program, a retainer-based health program, a concierge health program, a health insurance plan or policy, and the like.

Systems for Providing Remote Medical Therapy

In some embodiments, the devices and software applications disclosed herein are integrated into systems for providing remote medical diagnosis and therapy to a subject. In some embodiments, also disclosed are methods of using the devices, software applications, and systems for providing remote medical diagnosis and therapy to a subject. In various embodiments, the systems, devices, software applications, and methods disclosed herein are useful for providing remote medical diagnosis and therapy to a subject in a wide range of healthcare encounters. In further embodiments, the systems, devices, software applications, and methods disclosed herein are useful for providing remote medical diagnosis and therapy to a subject in convenient, semi-urgent, urgent, and/or emergent healthcare encounters. In various embodiments, the systems, devices, software applications, and methods disclosed herein are useful for providing remote medical diagnosis and therapy to a subject with acute, subacute, and/or chronic illnesses.

In some embodiments, the systems for providing remote medical diagnosis and therapy to a subject include a live, licensed healthcare provider, such as a telemedical care provider, located remotely from the subject.

In some embodiments, the systems for providing remote medical diagnosis and therapy to a subject include a networked device that includes at least one processor, at least one memory device, and an operating system configured to perform executable instructions. In some embodiments, the networked device is accessible to a subject. In further embodiments, the networked device includes hardware and software to facilitate telecommunications between the subject (and/or a caregiver) and a live, licensed healthcare provider located remotely from the subject. In still further embodiments, the system includes a medical therapy device with at least one USB connector and a confirmation component in communication with the networked device. In still further embodiments, the networked device and/or medical therapy device includes one or more biosensors. In still further embodiments, the networked device and/or medical therapy device includes an apparatus for dispensing one or more medical items from an inventory of medical items to a subject.

In some embodiments, the systems for providing remote medical diagnosis and therapy to a subject include a computer program including executable instructions operable to create an application. In various embodiments, the application includes one or more web applications, mobile applications, and/or compiled applications. In some embodiments, one or more computer programs are provided to the networked device. In some embodiments, one or more computer programs are provided to one or more remote computer systems, servers, and/or databases. In further embodiments, one or more computer programs are provided via a computer network. In various embodiments, the computer programs include one or more software modules. In some embodiments, a computer program includes a module for telecommunications between the networked device, or a user thereof, and a live, licensed healthcare provider. In some embodiments, a computer program includes a module for applying a diagnostic or therapeutic analysis. In various embodiments, the module for applying a diagnostic or therapeutic analysis predicts a health or economic outcome, predicts acute risks of a medical condition, with and without one or more potential therapies over various time periods. In some embodiments, a computer program includes a module for identifying subjects. In some embodiments, a computer program includes a module for identifying and/or verifying the credentials of healthcare providers. In some embodiments, a computer program includes a module for providing instantaneous encounter-specific financial insurance coverage. In further embodiments, the insurance coverage includes a level of guarantee and an associated premium.

In some embodiments, the systems, devices, and computer programs disclosed herein are monitored or supervised, to some extent, by a healthcare provider in real time. In further embodiments, the systems, devices, and software programs disclosed herein are operated by a healthcare provider in real time. In some embodiments, the systems, devices, and computer programs disclosed herein optionally operate in an unsupervised, or automated, mode. For example, in some embodiments, the systems, devices, and computer programs disclosed herein include an automated emergency mode. In further embodiments, an automated emergency mode is activated by subjective observations by a live, remote healthcare provider (e.g., choking, chest pain, etc.) or by objective measurements of a biosensor (e.g., blood O2 saturation of less than 88%). In still further embodiments, in an automated emergency mode, the systems, devices, and computer programs take autonomous actions, unsupervised by a live healthcare provider, including calling 911 or otherwise activating the emergency response system.

Many system configurations are contemplated herein and are suitable. In some embodiments, the system includes a networked device and/or a medical therapy device that is present with, or is accessible by, a subject. In further embodiments, the subject directly accesses the telecommunications features, biosensor features, medication dispensing features, and/or diagnostic or therapeutic analysis features of the system.

In other embodiments, the system includes a plurality of medical diagnostic devices. In further embodiments, the features of the system described herein are distributed among a plurality of devices in any suitable combination. For example, in some embodiments, a telecommunications module is housed in a separate device. By way of further example, in some embodiments, a medical therapy device is housed in a separate device. By way of further example, in some embodiments, a biosensor module is housed in a separate device. By way of further example, in some embodiments, a medication dispensing module is housed in a separate device. By way of further example, in some embodiments, a diagnostic or therapeutic analysis module is housed in a separate device. In other embodiments, the system includes one or more medical therapy devices with a reversibly separable, mobile component, which is present with, or is accessible by, a subject. In further embodiments, one or more of the telecommunications features, biosensor features, medication dispensing features in communications with a medical therapy device, and/or diagnostic or therapeutic analysis features of the device are included with a reversibly separable, mobile element.

In some cases, the biosensor or biosensors are present with, or is accessible by, the subject. In other cases, the biosensor or biosensors are in a different location from the subject in need of examination (such as a centralized, stationary installation) and the subject travels to this location for examination or to provide a fluid or tissue sample. In some cases, the apparatus, in communications with the medical therapy device, for dispensing medical items is present with, or is accessible by, the subject such that medical items are optionally dispensed directly to a subject or an appropriate caregiver. In other cases, the apparatus, in communications with the medical therapy device, for dispensing medical items is in a different location from the subject for whom items are intended (such as a centralized, stationary installation) and the items are dispensed remotely for the subject.

In some embodiments, the devices, systems, and software are intranet-based. In some embodiments, the devices, systems, and software are Internet-based. In further embodiments, the devices, systems, and software are World Wide Web-based. In still further embodiments, the devices, systems, and software are cloud computing-based. In other embodiments, the devices, systems, and software are based on data storage devices including, by way of non-limiting examples, CD-ROMs, DVDs, flash memory devices, RAM (e.g., DRAM, SRAM, etc.), ROM (e.g., PROM, EPROM, EEPROM, etc.), magnetic tape drives, magnetic disk drives, optical disk drives, magneto-optical drives, solid-state drives, and combinations thereof.

Referring to FIG. 1, in a particular embodiment, a remote healthcare system described herein is utilized for risk profiling and dispensing a medication to a subject. In this embodiment, a patient initiates contact with a remotely located telemedical care provider (including, for example, a telemedicologist or telemedicalist) 1. The telemedical care provider interviews the subject via a telecommunications ling to determine if a medical emergency exists 2 and whether or not to activate EMS. The telemedical care provider subsequently utilizes remote biosensors to collect biometric health data 3, which is integrated into a personalized risk assessment for the subject in order to facilitate diagnosis and prescription of a medication. Further in this embodiment, the telemedical care provider transmits an authorization for a short-term supply of a medication for the subject to a pharmacist 4. The pharmacist in turn activates an apparatus for remotely dispensing the medication to the subject 5. The telemedical care provider follows-up by issuing a prescription for a long-term supply of medication 6, which is filled by one of several traditional routes.

Figure 2:
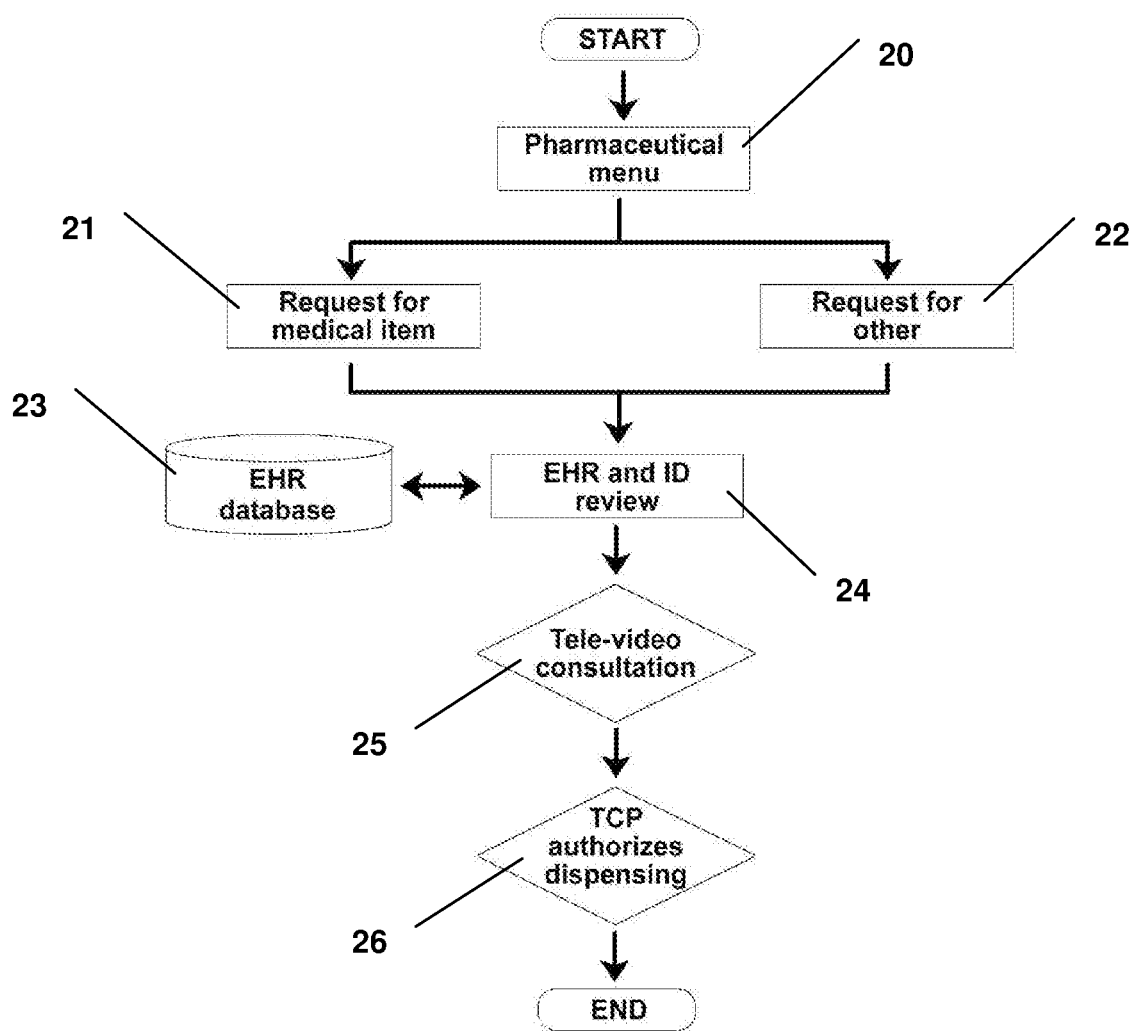
FIG. 2 shows a non-limiting example of a process flow for providing remote pharmacy services; in this case, a process including identification of a subject and review of their electronic health records, tele-video between a subject and a live, licensed healthcare provider, and subsequent authorization by the provider of dispensing a medical item.

Referring to FIG. 2, in a particular embodiment, remote pharmacy services are offered via presentation of a menu of pharmaceutical options 20. A subject alternatively requests dispensing of a particular medical item 21 or another request 22. Appropriateness of pharmaceutical requests requires query of an EHR database 23 and review of EHRs and subject identification information 24. An audio-video conference 25 between a subject and a remote healthcare provider (e.g., a pharmacist, etc.) further provides opportunity to assess the request and/or instruct a subject on use of the pharmaceutical. Further in this embodiment, a telemedical care provider 26 optionally authorizes dispensing of appropriate medical items from an apparatus for dispensing one or more medical items from an inventory of items risk profiled to a particular subject, family, population, venue, circumstance, or situation, which is in communication with the device and/or a networked device.

The inventions disclosed herein include business methods. In some embodiments, the devices, systems, software, and methods disclosed herein are marketed, advertised, and sold as, for example, products and services for providing remote medical diagnosis and therapy to a subject. The products and services disclosed herein are particularly well suited for providing low cost healthcare alternatives the uninsured, the underinsured, those in remote and rural areas, and those in developing countries. The products and services disclosed herein are also well suited for supplementation of existing healthcare systems in outpatient, urgent care, or acute situations. The products and services disclosed herein are also well suited for supplementation of existing healthcare systems in emergency, disaster, or combat situations.

In some embodiments, the devices, systems, and software are employed, in part or in whole, in healthcare facilities such as hospitals, hospice, nursing homes, urgent care offices, diagnostic laboratories, and the like. In some embodiments, the devices, systems, and software are employed, in part or in whole, in veterinary facilities such as animal hospitals, veterinary offices, and the like. In some embodiments, the devices, systems, and software are employed, in part or in whole, in a subject's home. In some embodiments, the devices, systems, and software are employed, in part or in whole, in retail businesses such as boutiques, clinics, pharmacies, drug stores, or supermarkets. In some embodiments, the devices, systems, and software are mobile and employed, in part or in whole, in vehicles used by, for example, EMS personnel (e.g., EMTs, paramedics, etc.), police, fire fighters, first responders, FEMA personnel, military personnel, etc. In some embodiments, the devices, systems, and software are mobile and elements are carried or worn by, for example, EMS personnel (e.g., EMTs, paramedics, etc.), police, fire fighters, first responders, FEMA personnel, military personnel, and the like.

In some embodiments, the devices, software, systems, and methods are further utilized to provide remote telemedical services. These services would, for example, improve the productivity of clinicians, relieve overburdened healthcare systems, and create healthcare alternatives for the uninsured, the underinsured, and those in remote areas and developing countries with limited access to telemedical, outpatient, acute care, urgent care, and insurance services.

In some embodiments, the devices, software, systems, and methods are further utilized to provide remote medical risk assessment and diagnostic services. These services would, for example, relieve overburdened healthcare systems in outpatient, acute care, and urgent care situations.

In some embodiments, the devices, software, systems, and methods are further utilized to provide remote insurance services providing, for example, instantaneous encounter-specific coverage including a level of guarantee and an associated premium.

In some embodiments, the devices, software, systems, and methods are utilized by contract research organizations (CROs), service organizations that provide support to the pharmaceutical and biotechnology industries in the form of research services outsourced on a contract basis. In further embodiments, the devices, software, systems, and methods are utilized to improve efficiency, reduce error, and improve the integrity of study data collected by a CRO. In further embodiments, the devices, software, systems, and methods are utilized by a CRO to facilitate the process of recruiting subjects for a research study. For example, in many cases CROs search for a very specific cohort of individuals who meet the inclusion criteria for a particular study. Many of these individuals may be remotely located and coming into a research center for the study would create an imposition for both the CRO and the individual. In such embodiments, remote technology such as that described herein improves the process for the CRO and the individual.

In some embodiments, the devices, software, systems, and methods are utilized in transitional care. In many cases, inadequate care coordination, including poor care transitions, result in wasteful spending and unnecessary hospital readmissions. When discharged from a hospital, patients often receive little information on how to care for themselves, when to resume activities, what medication side effects to look out for, and how to get answers to questions. Current and pending legislation creates powerful incentives for improving discharge methods and improving the quality of transitional care. In further embodiments, the devices, software, systems, and methods are utilized to provide follow up consultations with patients to ensure they understand post-care procedures, medication regimens, and for on-going analysis of the risk of readmission.

Subjects

In some embodiments, the systems, devices, software, and methods disclosed herein provide remote medical diagnosis and therapy to a subject. In further embodiments, a module for telecommunications provides communications between one or more healthcare providers and a subject. In further embodiments, at least one remotely controlled biosensor is used to examine a subject. In further embodiments, a software module applies a diagnostic or therapeutic analysis for a subject. In still further embodiments, diagnostic or therapeutic analysis involves accessing health and economic records for a subject. In further embodiments, an apparatus dispenses one or more medical items to a subject. In further embodiments, a software module provides instantaneous encounter-specific financial insurance coverage with a level of guarantee and an associated premium to a subject.

In some embodiments, the subject is a human medical patient. In further embodiments, the subject is a human, pediatric medical patient. In other embodiments, the subject is a human, adult or geriatric medical patient. In some embodiments, a human medical patient has one or more insurance policies for medical care.

In further embodiments, an insurance policy covers the events or conditions leading a subject to interact with the systems and devices described herein. In further embodiments, a human medical patient is under the care of a physician. In some embodiments, a human medical patient does not have an insurance policy for medical care. In further embodiments, no insurance policy covers the events or conditions leading a subject to interact with the systems and devices described herein. In further embodiments, a human medical patient is not under the care of a physician.

In some embodiments, the subject is a non-human animal veterinary patient. In further embodiments, a non-human animal subject is under the care of an owner, caretaker, rescuer, or veterinarian. In still further embodiments, a non-human animal subject includes, by way of non-limiting example, those attended to by exotic animal veterinarians, large animal veterinarians, domestic animal veterinarians, wildlife veterinarians, laboratory animal veterinarians, food animal veterinarians, and equine veterinarians. In still further embodiments, a non-human animal subject includes, by way of non-limiting example, those classified as invertebrates, fish, amphibians, reptiles, birds, and mammals.

In some embodiments, the systems, devices, and software disclosed herein include hardware and software modules for identifying a subject and/or determining or verifying the insurance coverage of a subject. In further embodiments, a subject enters identifying information via an input device (e.g., keyboard, keypad, touch screen, multi-touch screen, pointing device, microphone, video camera, etc.) associated with the systems and devices disclosed herein. In further embodiments, a subject presents a physical object such as an insurance card, credit card, driver's license, etc. In still further embodiments, a subject presents their person as a source of identifying information. In some embodiments, a module for identifying a subject utilizes personal information including, by way of non-limiting example, name, address, employer, date of birth, age, and the like. In some embodiments, a module for identifying a subject utilizes health insurance information including, by way of non-limiting example, payer, primary care physician, policy number, group number, name of insured, and the like. In some embodiments, a module for identifying a subject utilizes credit card information including, by way of non-limiting example, card issuer, primary account holder, name on card, billing name, billing address, account number, and the like. In some embodiments, a module for identifying a subject utilizes driver's license information including, by way of non-limiting example, name, license number, state of issuance, expiration date, and the like. In some embodiments, a module for identifying a subject utilizes biometric information including, by way of non-limiting example, retinal information, iris information, fingerprint information, palm print information, facial geometry information, voice information, and combinations thereof. In further embodiments, the module for identifying the subject utilizes at least one remotely controlled biosensor to obtain biometric information.

Healthcare Providers

In some embodiments, the systems, devices, software, and methods described herein utilize the services of a healthcare provider. In some embodiments, a healthcare provider is live. As used herein, the term "live" describes a human healthcare provider, as opposed to an artificial intelligence or a software algorithm, who interacts with the systems, devices, software, and/or subject described herein asynchronously, substantially synchronously, or synchronously (e.g., in real-time).

In some embodiments, a healthcare provider is remote. As used herein, the term "remote" describes a healthcare provider who is not present with a subject at the time healthcare services are rendered using the inventions described herein. In some embodiments, a remote healthcare provider is outside of the facility, city, county, state, or country of the subject at the time healthcare services are rendered using the inventions described herein.

In some embodiments, a healthcare provider is an adjunct provider. The term "adjunct" describes a healthcare provider who is credentialed by a licensed primary healthcare provider facility, group, or individual to provide remote care for one or more patients who are legally under the care of the primary provider. In some embodiments, the adjunct healthcare provider is a telemedical care provider.

In some embodiments, the methods, systems, and software described herein utilize the services of one or more telemedical care providers. In some embodiments, telemedicology refers to a branch of medicine or surgery requiring specialized, formal, peer-reviewed training as a specialty or subspecialty of medicine concerned with safely and efficaciously providing remote diagnosis and therapy via telemedicine technology and equipment. In some embodiments, formal training in telemedicology requires completion of a fellowship in telemedicology. In further embodiments, a telemedicologist is a physician, surgeon, dentist and/or veterinarian specialized in telemedicology and providing remote diagnosis and therapy via telemedicine technology and equipment. In still further embodiments, a telemedical care provider (TCP) is a healthcare worker trained and engaged in provision of remote diagnosis and therapy via telemedicine technology and equipment. In some embodiments, a TCP is, for example, a telemedicologist. In further embodiments, a TCP is a telemedicologist (e.g., physician, surgeon, dentist, veterinarian, or other licensed professional) who, following a residency and/or fellowship in their field, is board certified for example by the American board of surgery, medicine, pediatrics in primary care and or in a subspecialty such as cardiology, etc. In still further embodiments, a TCP is a telemedicologist (e.g., physician, surgeon, dentist, veterinarian, or other licensed professional) who is a certified by a recognized body providing a peer reviewed telemedicology education program. In some embodiments, a TCP is, for example, a licensed physician extender (e.g., nurse practitioner, physician assistant, registered nurse, pharmacist, licensed vocational nurse, emergency medical technician, etc.) directly supervised by or reporting to a telemedicologist in activity related to the provision of remote diagnosis and therapy via telemedicine technology and equipment. In some embodiments, a telemedicalist is a physician specialized in the delivery of telemedical care to acutely ill hospitalized subjects.

In some embodiments, a telemedical care provider is a doctorate level health care provider. In further embodiments, a telemedical care provider is a physician, dentist, or veterinarian telemedicologist. In other embodiments, a telemedical care provider is a non-physician. In further embodiments, a telemedical care provider is, by way of non-limiting examples, a pharmacist, a dentist, a physician assistant, a nurse practitioner, a registered nurse, a pharmacist, a chiropractor, an emergency medical technician, a licensed practical nurse, a certified ultrasound technician, a psychologist, a social worker, a military medic, a physical therapist, an occupational therapist, a speech therapist, a radiology technician, a cardiac catheterization technician, a clinical pathology laboratory technician, a medical aesthetician, a licensed medical technologist, a toxicologist consultant, a credentialed medical legal consultant, and a credentialed hospital operations administrator. In some embodiments, a telemedical care provider is a veterinarian or a veterinary nurse, assistant, or technician.

In some embodiments, the systems, devices, software, and methods described herein utilize the services of a plurality of healthcare providers. In further embodiments, a plurality of healthcare providers includes 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500 or more providers, including increments therein. In some embodiments, the systems, devices, software, and methods described herein utilize the services of at least 2, 3, 4, 5, 6, 7, 8, 9, 10, 11, 12, 13, 14, 15, 16, 17, 18, 19, 20 or more healthcare providers. In further embodiments, a plurality of healthcare providers use the systems simultaneously. In still further embodiments, a healthcare provider is identified or selected for a particular case or contact based on parameters including, by way of non-limiting examples, a patient's condition, disease, or injury, severity of a patient's condition, disease, or injury, a patient's insurance eligibility, or availability.

In some embodiments, the systems, devices, software, and methods described herein include hardware and a software module to verify a healthcare provider's identity. In further embodiments, a provider enters identifying information via an input device (e.g., keyboard, keypad, touch screen, multi-touch screen, pointing device, microphone, video camera, etc.) associated with the systems and devices disclosed herein. In further embodiments, a provider presents a physical object such as a driver's license, credit card, professional association card, etc. In still further embodiments, a provider presents their person as a source of identifying information. In some embodiments, a module for identifying a provider utilizes information including, by way of non-limiting example, personal information, medical license information, malpractice insurance information, credit card information, driver's license information, and biometric information. In some embodiments, the systems, products, programs, and methods described herein include hardware and a software module to biometrically verify a provider's identity. In further embodiments, the biometric hardware and software is adapted to recognize physiological characteristics including, by way of non-limiting examples, retinal information, iris information, fingerprint information, palm print information, facial geometry information, voice information, and combinations thereof.

In some embodiments, a healthcare provider operates one or more of the medical therapy devices, apparatus, and/or software modules of the systems and devices described herein. In further embodiments, a healthcare provider operates, by way of non-limiting examples, a biosensor, an apparatus for dispensing one or more medical items, hardware and software for telecommunications, software for applying a diagnostic or therapeutic analysis, software for providing access to one or more electronic health records for a subject, software for identifying a subject, and software for providing instantaneous encounter-specific financial insurance coverage. In other embodiments, a healthcare provider assists in the operation of one or more of the medical therapy devices and/or software modules described herein. In yet other embodiments, a healthcare provider supervises or oversees operation of one or more of the medical therapy devices and/or software modules described herein.

In some embodiments, the systems, devices, software, and methods described herein do not utilize the services of a live healthcare provider. For example, in some embodiments, the systems and devices described herein include a non-communication mode, described further herein. In further embodiments, the systems and devices described herein operate in a non-communication mode when communication protocols fail, when communication channels or signals fail or are lost, or when devices are placed in a location where one or more communication protocols, channels, or signals are unavailable. In a non-communication mode, a live, remote healthcare provider is unable to monitor, supervise, or operate components of a device. By way of further example, in some embodiments, the systems and devices described herein include an emergency mode, described further herein. In an emergency mode, in some embodiments, components of a system or device act autonomously, without monitoring, supervision, or operation by a live, remote healthcare provider.

Credentialing

In some embodiments, a live healthcare provider is licensed, for example, by one or more U.S. state medical boards, a branch of the U.S. Federal Government (e.g., the Veteran's Administration, Department of Health and Human Services, and the Department of Defense, etc.) or a foreign national government. In some embodiments, a live healthcare provider is insured for professional malpractice.

In some embodiments, a subject is under the care of a primary care provider. In further embodiments, an adjunct healthcare provider is credentialed by a subject's primary care provider. In still further embodiments, an adjunct healthcare provider is credentialed by a subject's primary care provider to provide, for example, remote diagnosis and therapy, telemedical services, urgent care services, outpatient services, acute care services, pharmacy services, or insurance services to the subject. In still further embodiments, the adjunct healthcare provider is identified or selected based on one or more of: type of patient's condition, severity of a patient's condition, a patient's insurance eligibility, or availability of one or more adjunct healthcare providers. In still further embodiments, a subject's primary care provider credentials more than one adjunct healthcare provider for a particular subject.

In other embodiments, a subject is under the care of a live healthcare provider described herein. In further embodiments, a live healthcare provider provides, for example, remote diagnosis and therapy, telemedical services, urgent care services, outpatient services, acute care services, pharmacy services, or insurance services to a subject. In appropriate circumstances, a live healthcare provider refers a subject to another healthcare provider. In appropriate circumstances, a live healthcare provider triages a subject to a higher level of care (e.g., inpatient care, emergency response system, etc.). In appropriate circumstances, a live healthcare provider triages a subject to a lower level of care (e.g., self-care, bed rest, oral hydration, etc.).

The systems, devices, software, and methods described herein include, in various embodiments, a software module for verifying the identity and/or credentials of a healthcare provider. In some embodiments, the software module creates, stores, and retrieves healthcare provider identity and credential records. In some embodiments, the software module verifies a credential issued by a licensed primary healthcare provider facility, group, or individual. In further embodiments, the primary healthcare provider facility, group, or individual is licensed, for example, by one or more U.S. state medical boards, a branch of the U.S. Federal Government (e.g., the Veteran's Administration, Department of Health and Human Services, and the Department of Defense, etc.) or a foreign national government. In further embodiments, a credential issued for a live, remote, adjunct healthcare provider to provide remote adjunct care for one or more patients legally under the care of said licensed primary healthcare provider facility, group, or individual. In some embodiments, a patient is admitted to the healthcare facility.

In other embodiments, a patient is not admitted to the healthcare facility. In further embodiments, a patient is receiving care as an outpatient or emergency department patient at the healthcare facility.

In some embodiments, the software module verifies a credential issued by a licensed primary healthcare provider facility, group, or individual that indicates the remote adjunct healthcare provider successfully completed a medical and legal screening process. In further embodiments, a screening process includes verification of, by way of non-limiting examples, prescription license, education, training, certifications, professional references, malpractice insurance coverage, malpractice insurance state, malpractice insurance coverage limits, legal license to practice their profession, and state of licensure. In still further embodiments, a screening process includes one or more live interviews of a remote adjunct healthcare provider by a licensed primary healthcare provider facility, group, or individual.

In some embodiments, the software module verifies a credential that indicates a licensed primary healthcare provider facility, group, or individual has granted admitting privileges to a remote adjunct healthcare provider. In further embodiments, admitting privileges include billing privileges. In some embodiments, admitting privileges include the right to admit patients to a facility for a specific diagnostic or therapeutic service. In some embodiments, admitting privileges include the right to admit patients to a facility for a consultative service. In some embodiments, admitting privileges are granted to a non-physician to treat patients independently with the appropriate states required oversight and review of the healthcare protocols used by a legally licensed, credentialed physician to empower the non-physician to execute healthcare.

Biosensors

In some embodiments, the systems for providing remote therapy to a subject includes a networked device including a processor, a memory, and an operating system configured to perform executable instructions and a medical therapy device in communications with an apparatus for dispensing one or more medical items from an inventory of medical items to a subject. In further embodiments, the networked medical therapy device includes one or more biosensors.

Any suitable biosensor is used with the systems, devices, software, and methods disclosed herein.

In some embodiments, a biosensor is a physicomechanical sensor. In further embodiments, a biosensor includes, by way of non-limiting examples, a thermometer, a scale, a blood pressure sensor, and a respirometer.

In some embodiments, a biosensor is a physicochemical sensor. In further embodiments, a biosensor includes physicochemical sensors for culturing and/or analyzing a tissue sample or a fluid sample such as blood, saliva, urine, mucus, hair, etc. In further embodiments, analysis includes qualitative analysis, such as detecting a property, detecting a substance, detecting a reaction, or detecting a pathogen. In further embodiments, analysis includes quantitative analysis, such as measuring a property, measuring a substance, measuring a reaction, or measuring a pathogen. In still further embodiments, a biosensor includes, by way of non-limiting examples, blood chemistry devices, urinalysis devices, blood glucose sensors, pulse oximeters, and the like.

In some embodiments, a biosensor is an imaging sensor. In further embodiments, an imaging sensor includes, by way of non-limiting examples, a video camera, a high definition video camera, a thermal imaging camera, a thermography device, magnetic resonance imaging (MRI) device, an ultrasound device (e.g., echocardiography, obstetrical sonography, intravascular ultrasound, etc.), and a tomography device (e.g., computed tomography (CT), computed axial tomography (CAT), etc.).

In some embodiments, a biosensor is an acoustic sensor. In further embodiments, a biosensor includes, by way of non-limiting examples, a stethoscope and specialized remote auscultation devices adapted for hearing gut sounds, heart sounds, or lung/breath sounds.

In some embodiments, a biosensor is a bioelectric sensor. In further embodiments, a biosensor includes, by way of non-limiting examples, an electrocardiography (ECG or EKG) device, a heart rate monitor, an electromyography (EMG) device, an impedance sensor, and a galvanic skin response sensor.

The networked medical devices described herein optionally utilize biosensors to perform a wide range of suitable diagnostic tests. In various embodiments, suitable diagnostic tests include, by way of non-limiting examples, blood sugar test (e.g., diabetes), complete blood count or CBC blood test (e.g., anemia, infection, etc.), troponin blood test (e.g., myocardial infarction), serum creatinine blood test (e.g., kidney function), Chem 7 blood test (e.g., nutritional status, electrolytes imbalances, etc.), ultrasound and fiber optic camera examination, spirometer test (e.g., asthma, COPD, etc.), INR blood test (e.g., Coumadin patient), urine test detecting blood (e.g., gross and microscopic hematuria), blood cholesterol test (e.g., hyperlipidemia), blood pressure test (intermittent vs. continuous) (e.g., hypertension or hypotension), pulse oximetry test (e.g., hypoxia, etc.), and temperature measurement (e.g., fever, etc.), and 12 lead EKG (e.g., myocardial infarction, arrhythmias, etc.).

Many modes of operation are suitable for biosensors used with the systems, devices, software, and methods disclosed herein.

In some embodiments, a biosensor operates in an automated mode. In further embodiments, an automated biosensor operates according to a pre-planned script or set of instructions without direction from a healthcare provider, an operator, or a subject. For example, a digital scale automatically weights a subject without instruction and records their weight.

In some embodiments, a biosensor operates in a subject-operated mode. In further embodiments, a subject directs or controls a bio sensor. For example, a subject places a wired electronic thermometer under their tongue and activates a control to begin a body temperature reading. In some embodiments, a subject operates a biosensor under instruction provided by a live, remote healthcare provider or a software application.

In some embodiments, a biosensor operates in a remotely controlled mode. In further embodiments, a healthcare provider directs or controls a bio sensor from a remote location. For example, a live healthcare provider uses a software application to remotely manipulate and position an autofocus, high definition video camera that is mounted on a robotic arm to examine a skin lesion on a subject's face. By way of further example, a live healthcare provider uses a software application to remotely manipulate and position an ultrasound probe to examine a subject's heart.

In some embodiments, a biosensor operates in a subject-operated mode and/or a remotely controlled mode and is further observed, assisted, or operated by technician. In further embodiments, a technician is present with the subject (e.g., onsite). For example, a live, remote healthcare provider remotely supervises and operates an ECG device to interpret the electrical activity of the heart of a subject. A technician present with the subject assists in connecting the electrodes to appropriate sites on the surface of the subject's skin.

In various embodiments, one or more biosensors are capable of operating in multiple modes described herein. In further embodiments, such a biosensor switches between modes at predetermined points in a procedure. In further embodiments, such a biosensor switches between modes upon request of a healthcare provider, an onsite technician a subject, or an appropriate caregiver. For example, a subject can position an ultrasound probe under the direction of a healthcare provider and then activate a control that shifts control of the probe to a live, remote healthcare provider to fine tune the positioning via remote robotic controls.

In some embodiments, a biosensor is permanently attached to a device or system described herein. In other embodiments, a biosensor is reversibly attached to a device or system described herein and communicates with the device or system via wireless protocols including, by way of non-limiting embodiments, infrared, Bluetooth, ZigBee, Wi-Fi, 3G/4G/LTE wireless protocols and NFC protocols. In other embodiments, a biosensor is reversibly attached to a device or system described herein. In further embodiments, a removable biosensor stores data in memory and the data is communicated to the device or system at a later time when the biosensor is reconnected to the device or system.

In some embodiments, the systems and devices described herein do not include permanent biosensors. In further embodiments, remote diagnosis and therapy is provided by way of, for example, the experience of one or more live healthcare providers, data contained in electronic records and databases (e.g., EHRs, medical literature, news, etc.), data communicated and input by a subject or an appropriate caregiver, software for predicting acute risks and health and/or economic outcomes of patients, potential therapies, and the like, including combinations thereof.

Telecommunications

In some embodiments, the systems, devices, software, and methods described herein include hardware and software elements for establishing, conducting, and maintaining telecommunications. In further embodiments, telecommunications are used by the devices and systems described herein, for example, to communicate with subjects, healthcare providers, and other users of the devices and systems via a networked device; to access electronic health records and other sources of information; to monitor, regulate, control, and exchange data with biosensors; to monitor, regulate, control, and exchange data with an apparatus for dispensing medical items; to monitor, regulate, control, and exchange data with a module for applying a diagnostic or therapeutic analysis; and to monitor, regulate, control, and exchange data with a module for providing instantaneous encounter-specific financial insurance coverage that includes a level of guarantee and an associated premium.

In some embodiments, a module for telecommunications creates a communications link. In further embodiments, communication links enable one-way, two-way, or multi-way communication. In various further embodiments, communication links enable communication via, by way of non-limiting examples, telephone, push-to-talk, audio conference, video conference, SMS, MMS, instant message, Internet bulletin board, blog, microblog, fax, Internet fax, electronic mail, VoIP, or combinations thereof. In some embodiments, one or more communications links are interactive and provide real-time (e.g., synchronous) or near real-time (e.g., asynchronous) two-way communication or transfer of data and/or information.

In some embodiments, a module for telecommunications creates multiple communications links. In various embodiments, a module for telecommunications creates 1, 2, 3, 4, 5, 6, 7, 8, 9, 10, 20, 30, 40, 50, 60, 70, 80, 90, 100 or more communications links, including increments therein. In further embodiments, multiple communications links are created and maintained serially, or one at a time. In other embodiments, multiple communications links are created and maintained in parallel, or simultaneously.

In some embodiments, the communications link enables a live, remote healthcare provider to communicate with one or more other parties and vice versa. In some embodiments, the communications link is between a live, remote healthcare provider and a subject or a group of subjects. In some embodiments, the communications link is between a live, remote healthcare provider and an onsite caregiver or group of caregivers. In further embodiments, an onsite caregiver is a person who has an interest in, or responsibility for, the health and welfare of a subject and is present with the subject at least once, intermittently, often, or full-time. Non-limiting examples of onsite caregivers include an employee of a subject, a member of a subject's family, a physician, a dentist, a physician assistant, a nurse practitioner, a registered nurse, a pharmacist, a chiropractor, a licensed practical nurse, a veterinarian, a veterinary technician, a certified ultrasound technician, radiology technician, a psychologist, a social worker, a physical therapist, an occupational therapist, a speech therapist, a cardiac catheterization technician, a clinical pathology laboratory technician, a medical aesthetician, a licensed medical technologist, a hospice worker, an emergency medical technician, a paramedic, a police officer, and a firefighter. In further embodiments, an onsite caregiver communicates with a live, remote healthcare provider on behalf of a subject or to describe the condition of the subject. In some embodiments, the communications link is between a live, remote healthcare provider and one or more medical product or service providers including, by way of non-limiting examples, pharmaceutical product providers, diagnostic service providers, and therapeutic service providers. In further embodiments, a live, remote healthcare provider communicates with one or more medical product or service providers regarding products or services that are prescribed or recommended for a patient or the costs associated with such products or services. In some embodiments, the communications link is between a live, remote healthcare provider and one or more consultants including, by way of non-limiting examples, medical consultants, legal consultants, insurance consultants, and financial consultants. In further embodiments, a live, remote healthcare provider communicates with one or more medical consultants regarding a subject's medical history, diagnosis, past, current, or contemplated therapies, or prognosis. In further embodiments, a live, remote healthcare provider communicates with one or more legal consultants regarding compliance with applicable laws, regulations, and rules. In further embodiments, a live, remote healthcare provider communicates with one or more insurance and financial consultants regarding a subject's eligibility, coverage, benefits, deductable, or payment status. In still further embodiments, multiple communications links are established with a plurality of providers and/or consultants to form a conference to remotely discuss the care of one or more subjects.

In various embodiments, the module for telecommunications utilizes many suitable communications channels. In some embodiments, the module for telecommunications utilizes wired or fiber optic telephone, wired or fiber optic Internet, Wi-Fi, and the like, including combinations thereof. In various embodiments, the module for telecommunications utilizes a wide array of suitable communications protocols. In some embodiments, the module for telecommunications utilizes wired communications protocols. In some embodiments, the module for telecommunications utilizes wireless communications protocols. In further embodiments, suitable communications protocols include, by way of non-limiting examples, 3G (3rd generation mobile telecommunications), 4G (4th generation mobile telecommunications), and geosynchronous and low Earth orbit (LEO) satellite, or combinations thereof. In further embodiments, suitable communications protocols include, by way of non-limiting examples, transmission control protocol/internet protocol (TCP/IP), hypertext transfer protocol (HTTP), hypertext transfer protocol secure (HTTPS), file transfer protocol (FTP), user datagram protocol (UDP), internet message access protocol (IMAP), post office protocol (POP), simple mail transfer protocol (SMTP), and simple network management protocol (SNMP), or combinations thereof. In further embodiments, suitable communications protocols include, by way of non-limiting examples, voice over Internet protocol (VoIP) and voice, or combinations thereof.

In some embodiments, the module for telecommunications includes hardware and software to allow communication via multiple, redundant communications protocols. In further embodiments, the module switches between protocols based on user preference, protocol availability, signal strength, and the like. In some embodiments, the systems and devices described herein include a non-communication mode, wherein a module for telecommunications does not operate. In further embodiments, the systems and devices described herein operate in a non-communication mode when communication protocols fail or when communication channels or signals fail or are lost. In still further embodiments, the systems and devices described herein operate in a non-communication mode when placed in a location where one or more communication protocols, channels, or signals are unavailable.

In some embodiments, the systems and devices described herein do not include telecommunications elements. In further embodiments, remote diagnosis and therapy is provided by way of, for example, the experience of one or more live healthcare providers, data stored locally, data communicated and input by a subject or an appropriate caregiver, data captured by biosensors, software for predicting acute risks and health and/or economic outcomes of a patients and potential therapies, and the like, including combinations thereof.

In some embodiments, the module for telecommunications provides a graphic representation of the subject and the live healthcare provider. In some embodiments, a graphic representation is two-dimensional. In other embodiments, a graphic representation is three-dimensional. In some embodiments, a three-dimensional graphic representation is a virtual reality environment. In some embodiments, the subject and the live healthcare provider are depicted similarly to their actual appearance. In further embodiments, the actual appearance of a healthcare provider is determined based on historic records such as personnel files or based real-time information captured by a digital camera, video camera, and/or microphone. In further embodiments, the actual appearance of a subject is determined based on historic records such as medical records or based real-time information captured by a digital camera, video camera, and/or microphone. In other embodiments, the subject and the live healthcare provider are depicted differently from their actual appearance. In further embodiments, a subject or a healthcare provider selects an appearance for the graphic representation. In some embodiments, a graphic representation depicts the subject and the live healthcare provider in a virtual medical setting. In further embodiments, a virtual medical setting is, by way of non-limiting example, a medical office, an examination room, a diagnostic facility, a medical laboratory, an ultrasound station, a classroom, and the like.

In some embodiments, the systems, devices, software, and methods described herein further comprise a software module for electronically recording communications conducted over one or more communications links. In further embodiments, the audio, video, health record data, financial record data, and insurance record data exchanged are recorded. In still further embodiments, recorded communications are used to ensure sound medical policies and procedures and compliance with applicable laws, regulations, and rules.

In some embodiments, the communication links meet applicable legal data security standards. In some embodiments, the communication links meet applicable legal patient privacy standards. In further embodiments, the applicable legal standards include, by way of non-limiting examples, the Health Insurance Portability and Accountability Act of 1996 and The Health Information Technology for Economic and Clinical Health Act of 2009. In some embodiments, live and/or recorded electronic communications are encrypted. In further embodiments, cryptographic protocols such as Secure Sockets Layer (SSL) or Transport Layer Security (TLS) are applied to Internet-based communications such as web traffic, electronic mail, Internet faxing, instant message, and VoIP.

Diagnostic or Therapeutic Analysis

In some embodiments, the systems, devices, software, and methods described herein include a software module for applying a diagnostic or therapeutic analysis. In some embodiments, a software module for applying a diagnostic or therapeutic analysis is used by a live healthcare provider. In further embodiments, a software module for applying a diagnostic or therapeutic analysis is supervised, monitored, or operated by any of the live healthcare providers described herein. In some embodiments, the software module for applying a diagnostic or therapeutic analysis supplements the professional judgment of a live healthcare provider. In other embodiments, a software module for applying a diagnostic or therapeutic analysis is configured to operate in an automated mode and does not require supervision, monitoring, or operation by a healthcare provider.

Medical Items

In some embodiments, disclosed herein are systems and devices comprising an apparatus for dispensing one or more medical items and methods of using the same. In some embodiments, the medical items are dispensed to a subject as described herein. In other embodiments, the medical items are dispensed to a caregiver, medical representative, guardian, or legal representative of a subject.

In some embodiments, the apparatus for dispensing medical items is in the same location as the subject for whom items are intended and the items are dispensed directly to the subject or an appropriate caregiver. In other embodiments, the apparatus for dispensing medical items is in a different location from the subject for whom items are intended and the items are dispensed remotely for the subject.

In some embodiments, the medical items are dispensed singly or individually. In other embodiments, the medical items are dispensed in limited numbers. In further embodiments, the medical items are dispensed loose, unpackaged, or in a temporary package such as a cup, tray, box, or envelope. In still other embodiments, the medical items are dispensed in bulk.

In some embodiments, the apparatus for dispensing one or more medical items includes an outer sleeve-like casing covering an inner drawer. In further embodiments, the sleeve-like casing includes an opening wherein a tapered cantilever and traction pad mechanism provide childproofing. In still further embodiments, the apparatus for dispensing one or more medical items includes a unique identifier on a chip and a data port (e.g., mini-USB, micro-USB, Type A or B USB, etc.) forming a part of the inner drawer for confirmation and verification of the correct medication when in communication with the medical therapy device. In still further embodiments, the apparatus for dispensing one or more medical items includes an integrated memory chip for tracking and recording events.

In some embodiments, the medical items are pre-packaged. In further embodiments, pre-packaged medical items are sealed in a container (e.g., a package, etc.) prior to introduction to the dispensing apparatus. In other embodiments, pre-packaged medical items are sealed in a container (e.g., a package, etc.) prior to dispensing. In further embodiments, the container has a sterile interior. In further embodiments, the container is designed to prevent opening by a child (e.g., child-resistant, child-proof, etc.). Many containers are suitable for the medical items and include, by way of non-limiting examples, bottles, blister packaging, boxes, envelopes, and the like, each composed of one or more of several suitable materials that include, for example, plastic, foil, paper, cardstock, cardboard, Mylar, and the like. In some embodiments a locking mechanism will be in place to prevent opening of the medication container until the identity of the medication is verified by the software and device. These embodiments can include and are not limited to a closed loop circuit that once opened, the circuit becomes open and alerts the software that the medication has been opened. Additionally, a shape memory alloy that can change configuration due to temperature, ninitol, would be employed to prevent opening until the use of the device causes a shift in temperature and allows the opening of the container. Another embodiment would include a cantilever that is positioned in front of the opening of the container that is mechanically moved when the device correctly identifies the medication. In still further embodiments, the apparatus for dispensing medicaments itself is contained within a tamper proof package. In some embodiments, a container (e.g., a package, etc.) includes printed text. In further embodiments, the text is printed directly on the container. In other embodiments, the text is printed on a label that is applied to the container. In various embodiments, the printed text indicates, by way of non-limiting examples, the nature of the medical item or items, the identity of the items, the number of items, the use of the items, instructions for use, warnings, and the like. In various further embodiments, where the medical item is a prescription or non-prescription pharmaceutical, the printed text indicates, by way of non-limiting examples, drug name, dosage, expiration date, lot number, and the like. In various further embodiments, the printed text is customized and indicates, by way of non-limiting examples, the name of the subject, the address of the subject, the name of the prescribing professional or entity, and the address of the prescribing professional or entity, and the like. In some embodiments, the printed text is supplemented by graphics, photographs, or pictograms indicating the same.

In some embodiments, the inventory of medical items is risk profiled to a particular subject, population, venue, situation, or a combination thereof. In further embodiments, the inventory of medical items is determined by profiling health and/or economic risk for a subject or a population in advance of need for said medical items. In still further embodiments, software for applying a diagnostic or a therapeutic analysis disclosed herein is utilized to predict health or economic outcomes for a subject, a population, a venue, a situation, or a combination thereof in order to determine a risk profiled inventory of medical items. In some embodiments, the inventory of medical items is determined by performing a diagnostic or therapeutic analysis for a subject, a family, a population, a venue, a situation, or a combination thereof. In further embodiments, the inventory of medical items is determined by performing statistical analysis, performing probability calculations, making recommendations, and making outcome predictions to predict a health or economic outcome of a patient or therapy, wherein said prediction is real-time, individualized, and probabilistic-based and uses historic, peer reviewed health or economic data and emerging health or economic data. In some embodiments, the inventory of medical items is determined by performing a diagnostic or therapeutic analysis for a subject, a family, a population, a venue, a situation, or a combination thereof. In further embodiments, the inventory of medical items is determined by predicting acute risks, with and without one or more potential therapies, based on the severity of a condition and risks associated with each potential therapy to determine the intensity of therapy recommended.

In certain embodiments where an inventory of medical items is risk profiled to a particular subject, the inventory is determined by predicting future health and/or economic risks to the subject. In further embodiments, the inventory comprises or is enriched with medical items selected for their potential utility to the subject. In still further embodiments, the inventory comprises medical items not currently utilized by the subject. In some embodiments, the medical items are pre-prescribed to the subject as PRN (i.e., pro re nata, meaning "as needed") medications. In certain embodiments where an inventory of medical items is risk profiled to a particular family, the inventory is determined by predicting future health and/or economic risks to the members of the family. In further embodiments, the inventory comprises or is enriched with medical items selected for their potential utility to the members of the family. In still further embodiments, the inventory comprises medical items not currently utilized by any member of the family. In some embodiments, the medical items are pre-prescribed to the one or more members of the family as PRN (i.e., pro re nata, meaning "as needed") medications. In certain embodiments where an inventory of medical items is risk profiled to a particular population of subjects, the inventory is determined by predicting future health and/or economic risks to the population of subjects. In further embodiments, the inventory comprises or is enriched with medical items selected for their potential utility to the population. In certain embodiments where an inventory of medical items is risk profiled to a particular venue or location, the inventory is determined by predicting future health and/or economic risks to individuals present at the venue or location. In further embodiments, the inventory comprises or is enriched with medical items selected for their potential utility to individuals present at the venue or location. In certain embodiments where an inventory of medical items is risk profiled to a particular situation or circumstance, the inventory is determined by predicting future health and/or economic risks to individuals in the situation or circumstance.

In some embodiments, the inventory of medical items is delivered before it is needed based on anticipated need. In further embodiments, anticipated need is based on statistical level of likelihood that the items will be needed in the short-term future. In further various embodiments, anticipated need is based on statistical level of likelihood that the items will be needed within, by way of non-limiting examples, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more days, including increments therein. In further various embodiments, anticipated need is based on statistical level of likelihood that the items will be needed within, by way of non-limiting examples, 1, 2, 3, 4, 5, 6, 7, 8, 9, 10, 11, 12, 13, 14, 15, 16, 17, 18, 19, 20, 21, 22, 23, 24 or more months, including increments therein. In some embodiments, ahead in time delivery enables the systems, devices, and methods described herein to provide real in time therapy.

Many types of medical items are suitable for dispensing to the subjects described herein. In various embodiments, the medical items include, by way of non-limiting examples, vitamins, minerals, dietary supplements, herbal remedies, over-the-counter medications, prescription medications, therapeutic devices, diagnostic devices, diagnostic kits, and educational materials.

In some embodiments, medical items include one or more vitamin supplement. In various further embodiments, suitable vitamin supplements include vitamin A (e.g., retinol), vitamin B1 (e.g., thiamine), vitamin B12 (e.g., cyanocobalamin, hydroxycobalamin, and methylcobalamin), vitamin B2 (e.g., riboflavin), vitamin B3 (e.g., niacin and niacinamide), vitamin B5 (e.g., pantothenic acid), vitamin B6 (e.g., pyridoxine, pyridoxamine, and pyridoxal), vitamin B7 (e.g., biotin), vitamin B9 (e.g., folic acid), vitamin C (e.g., ascorbic acid), vitamin D (e.g., cholecalciferol), vitamin E (e.g., tocopherols and tocotrienols), and vitamin K.

In some embodiments, medical items include one or more mineral supplement. In various further embodiments, suitable mineral supplements include, by way of non-limiting examples, calcium, chromium, iodine, iron, magnesium, phosphorus, potassium, selenium, and zinc.

In some embodiments, medical items include one or more dietary supplement. In various further embodiments, suitable dietary supplements include, by way of non-limiting examples, enzymes, herbs, and amino acids.

In some embodiments, medical items include one or more herbal remedies. In various further embodiments, suitable herbal remedies include, by way of non-limiting examples, Acai (*Euterpe oleracea*), Alfalfa (*Medicago sativa*), Aloe vera, Arnica (*Arnica montana*), Asthma weed (*Euphorbia hirta*), Astragalus (*Astragalus propinquus*), Barberry (*Berberis vulgaris*), Belladonna (*Atropa belladonna*), Bilberry (*Vaccinium myrtillus*), Bitter leaf (*Vernonia amygdalina*), Black cohosh (*Actaea racemosa*), Blessed thistle (*Cnicus benedictus*), Burdock (*Arctium lappa*), Cat's claw (*Uncaria tomentosa*), Cayenne (*Capsicum annuum*), Celery (*Apium graveolens*), Chamomille (*Matricaria recutita* and *Anthemis nobilis*), Chaparral (*Larrea tridentata*), Chasteberry (*Vitex agnus-castus*), Chili (*Capsicum frutescens*), Coffee senna (*Cassia occidentalis*), Comfrey (*Symphytum officinale*), Cranberry (*Vaccinium macrocarpon*), Dandelion (*Taraxacum officinale*), Digitalis (*Digitalis lanata*), Dong quai (*Angelica sinensis*), Elderberry (*Sambucus nigra*), Ephedra (*Ephedra sinica*), Eucalyptus (*Eucalyptus globulus*), European Mistletoe (*Viscum album*), Evening primrose (*Oenothera* species), Fenugreek (*Trigonella foenum-graecum*), Feverfew (*Tanacetum parthenium*), Flaxseed (*Linum usitatissimum*), Garlic (*Allium sativum*), Ginger (*Zingiber officinale*), Gingko (*Gingko biloba*), Ginseng (*Panax ginseng* and *Panax quinquefolius*), Goldenseal (*Hydrastis canadensis*), Guava (*Psidium guajava*), Hawthorn (*Crataegus laevigata*), Hoodia (*Hoodia gordonii*), Horse chestnut (*Aesculus hippocastanum*), Horsetail (*Equisetum arvense*), Jamaica dogwood (*Piscidia erythrina* or *Piscidia piscipula*), Kava (*Piper methysticum*), Konjac (*Amorphophallus konjac*), Lavender (*Lavandula angustifolia*), Licorice root (*Glycyrrhiza glabra*), Marigold (*Calendula officinalis*), Marsh mallow (*Althaea officinalis*), Milk thistle (*Silybum marianum*), Neem (*Azadirachta indica*), Noni (*Morinda citrifolia*), Papaya (*Carica papaya*), Peppermint (*Mentha× piperita*), Purple coneflower (*Echinacea purpurea*), Red clover (*Trifolium pratense*), Sage (*Salvia officinalis*), St. John's wort (*Hypericum perforatum*), Saw palmetto (*Serenoa repens*), Tea tree oil (*Melaleuca alternifolia*), Thunder God Vine (*Tripterygium wilfordii*), Turmeric (*Curcuma longa*), Valerian (*Valeriana officinalis*), White willow (*Salix alba*), Yerba santa (*Eriodictyon crassifolium*), and Yohimbe (*Pausinystalia yohimbe*).

In some embodiments, medical items include one or more medications. In further embodiments, the medical items include common medications such as insulin, oral hypoglycemics, diuretics, potassium, antibiotics, ACE inhibitors, other anti-hypertensives, anti-arrhythmics, anti-coagulants, anti-inflammatories, analgesics, oral vaccines, injectable vaccines, bronchodilators, steroids, and oxygen.

In some embodiments, medications include one or more over-the-counter (OTC) medications. OTC medications are those that may be sold directly to a consumer without a prescription from a healthcare professional. In further embodiments, OTC medications include, by way of non-limiting examples, allergy prevention treatment medications, antacid medications, anticandial medications, antihistamines, antidiarrheal medications, anti-fungal medications, anti-itch lotions and creams, asthma medications, cold sore/fever blister medications, contact lens solutions, cough suppressants, decongestants, nasal decongestant and cold remedies, diaper rash ointments, eye drops for allergy or cold relief, first aid supplies, hemorrhoid treatments, internal analgesics and antipyretics, liniments, menstrual cycle medications, migraine medications, motion sickness medications, nicotine gum or patches and smoking cessation aids, pediculicides, poison ivy protection medications, toothache and teething pain medications, and wart removal medications, not requiring a valid prescription.

In some embodiments, medications include one or more prescription medications. Prescription medications are those that may be sold only to consumers possessing a valid prescription. In some embodiments, a valid prescription is issued by a Doctor of Medicine (MD), Doctor of Osteopathic Medicine (DO), Physician Assistant (PA), Doctor of Optometry (OD), Doctor of Podiatry (DPM), Doctor of Naturopathic Medicine (NMD or ND), Doctor of Veterinary Medicine (DVM), Doctor of Dental Surgery (DDS), Doctor of Dental Medicine (DMD), Medical Psychologist, Nurse Practitioner (NP) or other Advance Practice Nurse. In further embodiments, prescription medications include, by way of non-limiting examples, ADHD medications, antacid medications (e.g., proton pump inhibitors), antibiotics, anticoagulants, antifungals, antipsychotics, antivirals, asthma and COPD medications, cholesterol-lowering medications (e.g., statins), contraceptives, depression medications, diabetes medications, erectile dysfunction medications, glaucoma medications, hormone therapy medications, hypertension medications, hypnotics, migraine medications, multiple sclerosis medications, nasal allergy medications, nausea medications, oral allergy medications, osteoporosis medications, overactive bladder medications, pain relief medications, rheumatoid arthritis medications, sedatives, and seizure medications, requiring a valid prescription.

In some embodiments, a live, licensed healthcare provider monitors, supervises, or operates, an apparatus for dispensing one or more medical items. In some embodiments, the live, licensed healthcare provider is a licensed pharmacist. In other embodiments, the live, licensed healthcare provider is in communication with a licensed pharmacist. In further embodiments, the live, licensed healthcare provider is responsible for monitoring, supervising, or operating the apparatus for dispensing medical items uses a software module for telecommunications to contact, conference, or otherwise communicate with a licensed pharmacist. In still further embodiments, the pharmacist assures the accuracy of the prescription and the medical items selected for dispensing to fill the prescription, reviews the prescription for recalls and drug interactions, etc. In some embodiments, the live, licensed healthcare provider is in communication with pharmacy technician supervised by a licensed pharmacist.

In certain embodiments, disclosed herein are systems and devices for providing remote medical diagnosis and therapy to subjects who have an injury or illness that requires immediate care but is not serious enough to warrant a visit to an emergency department. Accordingly, in some embodiments, the medical items are packaged to address the urgent need and contain a short-term supply of, for instance, medication. By way of example, in various embodiments, each package of medication contains less than a two-week supply of medication, less than a one-week supply of medication, less than a four-day supply of medication, and less than a two-day supply of medication.

In some embodiments, the opening of the apparatus for dispensing one or more medical items creates a signal identifying this event. In this embodiment, a closed loop circuit will form a part of the opening where the one or more medical items will be dispensed. Upon opening, the closed loop circuit will be broken creating an open circuit recognized by the medical therapy device. In certain embodiments, the open circuit will be recognized by the apparatus for dispensing one or more medical items and will send the information to the wireless enabled medical therapy device and allow the transmission of this information to the pharmacy and/or electronic medical record. In certain other embodiments, the medical therapy device will recognize the open circuit upon connecting to the apparatus for dispensing one or more medical items and send this information to the interfacing device (e.g., computer, tablet device, mobile phone, etc.) in order to update the patient's electronic medical record.

In some embodiments, the inventory of medical items comprises one or more therapeutic devices. In further embodiments, the therapeutic devices include, by way of non-limiting examples, first aid supplies, hearing aids, optical aids, prostheses, mobility aids, continuous positive airway pressure (CPAP) supplies, and the like. In some embodiments, the therapeutic devices include implements for administering medications such as syringes, needles, inhalers, infusers, and vaporizers.

In some embodiments, the inventory of medical items comprises one or more diagnostic devices. In further embodiments, the diagnostic devices include, by way of non-limiting examples, blood chemistry testing devices, hemoglobin testing devices, hematocrit testing devices, blood glucose testing devices, blood cholesterol testing devices, blood pressure testing devices, heart rate monitors, urinalysis devices, and sexually transmitted disease testing devices. In still further embodiments, the diagnostic devices include disposable parts and consumable supplies for the devices disclosed herein including, by way of non-limiting examples, test strips, reagents, solutions, and the like.

In some embodiments, the inventory of medical items comprises one or more diagnostic kits. In further embodiments, the diagnostic kits include, by way of non-limiting examples, blood chemistry testing kits, hemoglobin testing kits, hematocrit testing kits, blood glucose testing kits, blood cholesterol testing kits, urinalysis kits, and sexually transmitted disease testing kits.

In some embodiments, the medical items are dispensed from an inventory of medical items. The devices disclosed herein, in certain embodiments, vary widely in scale including, for example, portable devices, desktop devices, kiosk devices, and stationary devices, and installations Accordingly, a wide range of inventory sizes are suitable. In various embodiments, an inventory of medical items includes, by way of non-limiting example, about 1 to about 10, about 10 to about 100, about 100 to about 1,000, about 1,000 to about 10,000, about 10,000 to about 100,000 or more medical items, including increments therein. In various further embodiments, an inventory of medical items includes, by way of non-limiting example, 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500 or more types of medical items, including increments therein. In still further various embodiments, an inventory of medical items includes, by way of non-limiting example, 1, 2, 3, 4, 5, 6, 7, 8, 9, 10, 15, 20, 25, 30, 35, 40, 45, 50, 55, 60, 65, 70, 75, 80, 85, 90, 95, 100 or more variations of each medical item in the inventory, including increments therein. In some embodiments, an apparatus for dispensing one or more medical items includes features adapted to facilitate refilling, restocking, or resupplying the medical items or the inventory of medical items.

Devices for Providing Remote Medical Therapy

In some embodiments, a medical therapy device comprising at least one connector in communication with an apparatus for dispensing one or more medical items from an inventory of medical items to a subject is included in a system for providing remote therapy to a subject. In further embodiments, the systems include one or more networked devices that include at least one processor, at least one memory device, and an operating system configured to perform executable instructions. In still further embodiments, the medical therapy device is in communication with a networked device. In further embodiments, a networked device includes a software module for establishing, maintaining, and conducting telecommunications. In further embodiments, the systems disclosed herein include one or more biosensors. In still further embodiments, the biosensors are remotely controlled. In further embodiments, a medical therapy device includes a software module for applying a diagnostic or therapeutic analysis. In further embodiments, the medical therapy device includes an apparatus for dispensing one or more medical items from an inventory of medical items to a subject. In still further embodiments, a medical therapy device includes a software module for providing financial insurance coverage to a subject. In still further embodiments, a medical therapy device includes a software module for providing instantaneous encounter-specific financial insurance coverage with a level of guarantee and an associated premium to a subject.

The devices described herein are characterized by scalability. In various embodiments, the devices described herein have a wide range of suitable scales and sizes. Those of skill in the art will recognize that the most suitable scale for a particular application varies with, for example, the need for portability, tolerance of expense, the number and type of features desired, the amount and number of days of therapy required, the volume of subjects served, and the like.

In some embodiments, the medical therapy device is linked to a networked device that is a digital processing device and includes one or more hardware central processing units (CPU) that carry out the device's functions. In further embodiments, the networked device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the medical therapy device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random access memory (DRAM). In some embodiments, the non-volatile memory comprises ferroelectric random access memory (FRAM). In some embodiments, the non-volatile memory comprises phase-change random access memory (PRAM). In further embodiments, the storage and/or memory capabilities are a combination of devices such as those disclosed herein.

In some embodiments, the medical therapy device includes a microphone and/or speaker to capture or send voice or other sound input or output. In other embodiments, the device includes a video camera to capture motion or visual input. In still further embodiments, the device includes a visual component (e.g., LED, etc.) to output visual confirmation. In still further embodiments, the device is a combination of devices such as those disclosed herein. In some embodiments, the input/output hardware and software is adapted to accommodate subjects, caregivers, healthcare providers, and other users with mental and physical disabilities.

In some embodiments, the medical therapy device communicates with the networked device and/or the apparatus for dispensing one or more medical items from an inventory of medical items via wireless protocols including, by way of non-limiting embodiments, infrared, Bluetooth, ZigBee, Wi-Fi, 3G/4G/LTE wireless protocols, RFID and NFC protocols. NFC protocols may be used alone or in combination with other wireless protocols to remove the need for performing scans to identify the networked device, entering passcodes, and removing the risk of establishing a connection with the wrong networked device accommodating those with mental and physical disabilities. In still further embodiments, the medical therapy device communicates with the networked device and/or the apparatus for dispensing one or more medical items from an inventory of medical items via a two-way pager system utilizing internal transmitters. Those of skill in the art will recognize the most appropriate components necessary to facilitate communication between the medical therapy device and the networked device and/or the apparatus for dispensing one or more medical items.

In some embodiments, Bluetooth, near field communication, or software developed protocols will be integrated into the device to allow a networked device, mobile apparatus and/or the apparatus for dispensing one or more medical items from an inventory of medical items and the device to send or receive information between one another. In order to allow communication between two specific entities so that the device is not communicating with all mobile devices in the area, both devices need to be programmed with each other's specific radio address. Utilizing Bluetooth, the device will broadcast its address, allowing the mobile apparatus, networked device, and/or the apparatus for dispensing one or more medical items to recognize this address and ask the user for confirmation of the use of this device. When this confirmation is received, the mobile apparatus, networked device, and/or the apparatus for dispensing one or more medical items will send its unique address to the device, thereby enabling communication between the two entities. In some embodiments, utilized NFC allows both devices to read the RFID tag of each other and therefore allow communication by themselves, resulting in transfer of data without requiring the user to allow access. Additionally, since the device requires the mobile apparatus or networked device's software to enable connection to the cloud information system for prescription information, etc., the cloud may be preloaded with the address of the device, allowing the mobile apparatus or networked device to retrieve the device's address upon login and then automatically "pair" the two allowing data transfer.

In accordance with the description herein, suitable networked devices include (or are based on), by way of non-limiting examples, server computers, desktop computers, laptop computers, notebook computers, subnotebook computers, netbook computers, netpad computers, set-top computers, handheld computers, Internet appliances, mobile smartphones, tablet computers, personal digital assistants, cable television boxes, satellite television boxes, land phones, mobile phones, and video game consoles. Those of skill in the art will recognize that many smartphones are suitable for use in the system described herein. Those of skill in the art will also recognize that select televisions and select digital music players with computer network connectivity are suitable for use in the system described herein. Suitable tablet computers include those with booklet, slate, and convertible configurations, known to those of skill in the art.

In some embodiments, the medical therapy device includes at least one USB connector. The at least one USB connector is reversibly retractable within a housing and extendable when needed to interface with a networked device, bio sensor, and/or apparatus for dispensing one or more medical items. In further embodiments, the at least one USB connector forms a part of the housing on a swivel to prevent damage to the compatible USB port of the networked device, biosensor, and/or apparatus for dispensing a medicament. In still further embodiments, connection via a USB cable facilitates connecting the medical therapy device to a compatible USB port of the networked device, biosensor, and/or apparatus for dispensing a medicament. In still further embodiments, the medical therapy device facilitates communication and data transfer with a technology device and/or the apparatus for dispensing one or more medical items by a method selected from at least one member of the group consisting of: audio port, microphone jack, USB mini/micro-connector, USB Type A or Type B connector, infrared, Bluetooth, ZigBee, Wi-Fi, 3G/4G/LTE wireless protocols, RFID, and NFC protocols.

In some embodiments, power is supplied to the medical therapy device and/or apparatus for dispensing medicaments via a USB interface with the networked device. In other embodiments, power is supplied to the medical therapy device and/or apparatus for dispensing medicaments directly from a wall socket, a phone land line or the like. In still further embodiments, the medical therapy device and/or apparatus for dispensing medicaments is powered by a rechargeable lithium ion battery, battery or the like.

In some embodiments, one or more components of a medical therapy device are reversibly separable. For example, in a particular embodiment, one or more biosensors are reversibly separable from a device to increase portability and facilitate access to subjects who may be immobile or isolated. In another particular embodiment, the telecommunications component is reversibly separable from the device to increase portability and facilitate communication with subjects who may be immobile or isolated. In another particular embodiment, the device is reversibly separable from the apparatus for dispensing medical items, again to increase portability, in cases where the dispensing apparatus is large, heavy, bulky, or fixed to a particular location. In other embodiments, the components are not separable.

Figure 3:
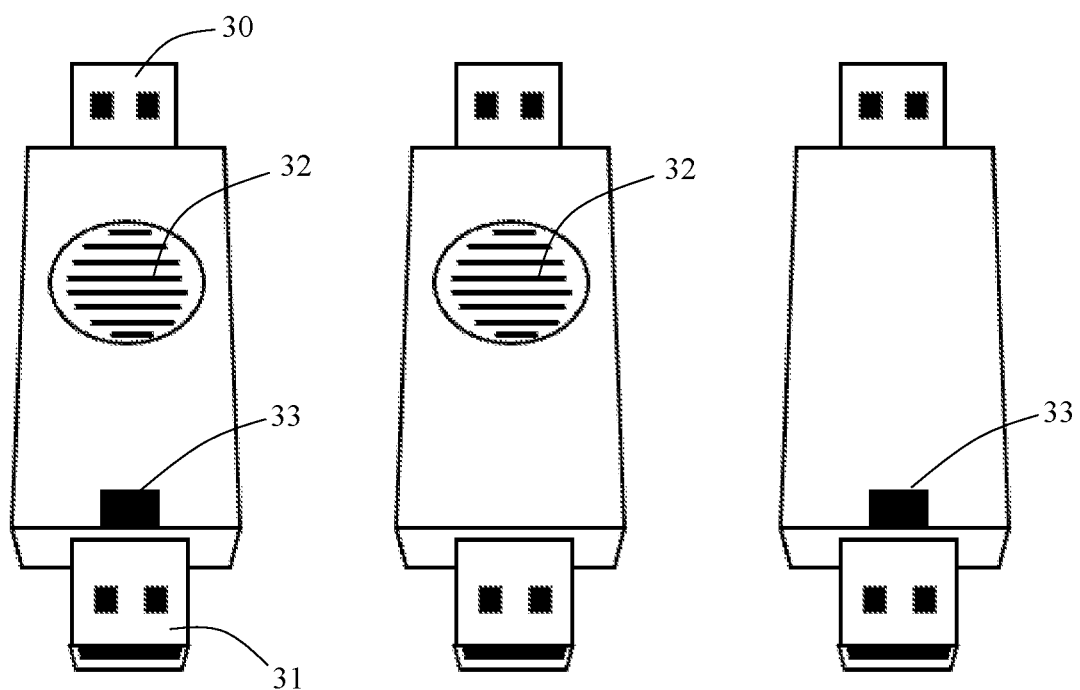
FIG. 3 shows a non-limiting example of a device for providing remote medical therapy to a subject in a healthcare encounter; in this case, a device including two USB connectors and visual and/or audio confirmation components or a combination thereof.

Referring to FIG. 3, in a particular embodiment, a connector device as described herein includes at least one USB connector 30, 31. The USB connector is constructed according to ordinary and known industry standards and may be a standard Type A or Type B USB connector or mini-USB or micro-USB connector. In this embodiment, the device includes at least one confirmation component. The at least one confirmation component optionally provides a visual confirmation, audible confirmation or a combination thereof. An audible confirmation component 32 is configured to provide audible confirmation that the apparatus for dispensing one or more medical items from an inventory of medical items in communication with the device contains the correct medicament identified by the telemedical care provider for the subject. In an alternative embodiment, a visual component 33 is configured to provide visual confirmation that the apparatus for dispensing one or more medical items from an inventory of medical items in communication with the device contains the correct medicament identified by the telemedical care provider for the subject.

Figure 4:
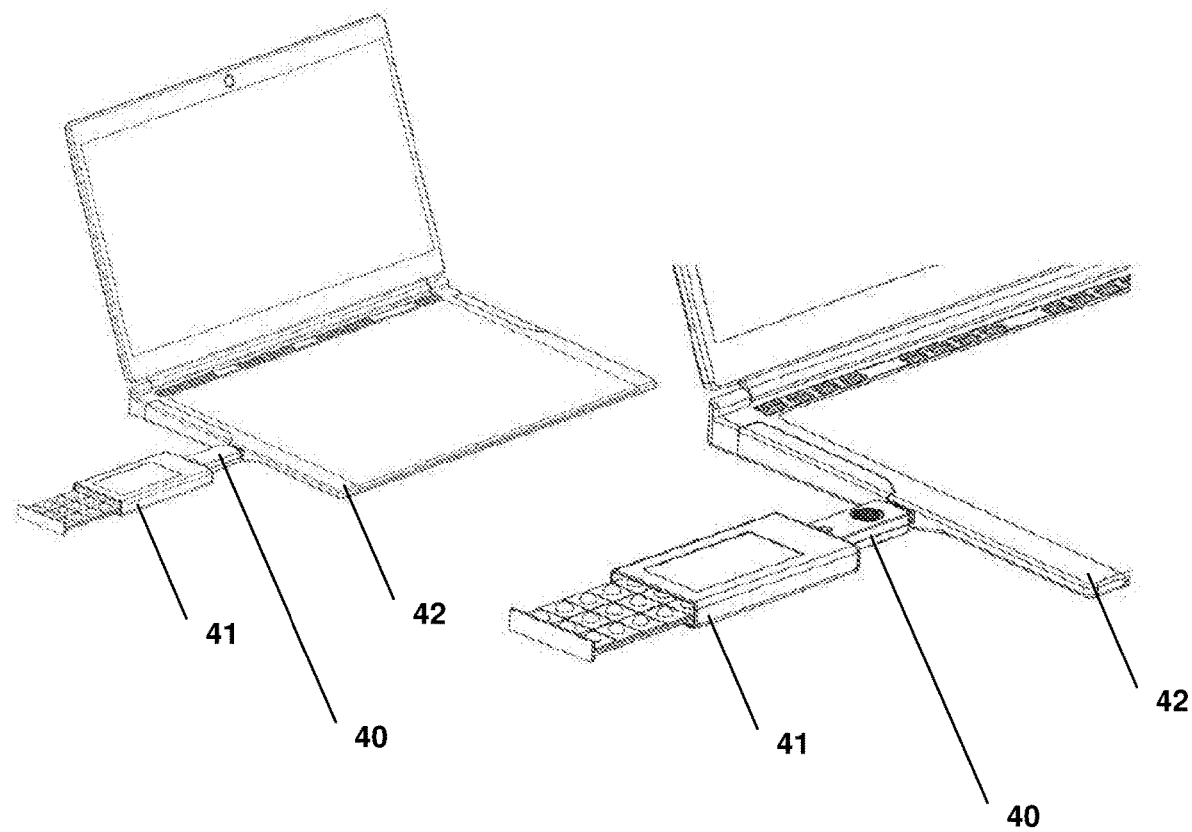
FIG. 4 shows a non-limiting example of a system for providing remote medical therapy to a subject in a healthcare encounter; in this case, a technology device connected to an apparatus for dispensing medicaments via a USB connector device.

Referring to FIG. 4, in a particular embodiment, a system for providing remote medical therapy to a subject in a healthcare encounter includes a networked laptop computer 42 running software applications to facilitate communications between a telemedical care provider and a subject or a subject's caregiver. In this embodiment, the laptop is connected via a USB interface to a connector device 40. The connector device 40 is also connected to an apparatus for dispensing medicaments 41. The connector device, in this case, provides communication between the laptop computer 42 and the apparatus for dispensing medicaments 41 such that a live, remote telemedical care provider can monitor and/or operate the dispensing apparatus.

The networked device may be server computers, desktop computers, laptop computers, notebook computers, sub-notebook computers, netbook computers, netpad computers, set-top computers, handheld computers, Internet appliances, mobile smartphones, tablet computers, personal digital assistants, television or satellite cable boxes, land phones, mobile phones, and video game consoles. Additionally, the networked device may be configured to include diagnostic modules that are removable and interchangeable such that the networked device is optionally configured for a wide range of environments, end users, and/or patient populations by selecting and installing particular diagnostic modules.

Figure 5:
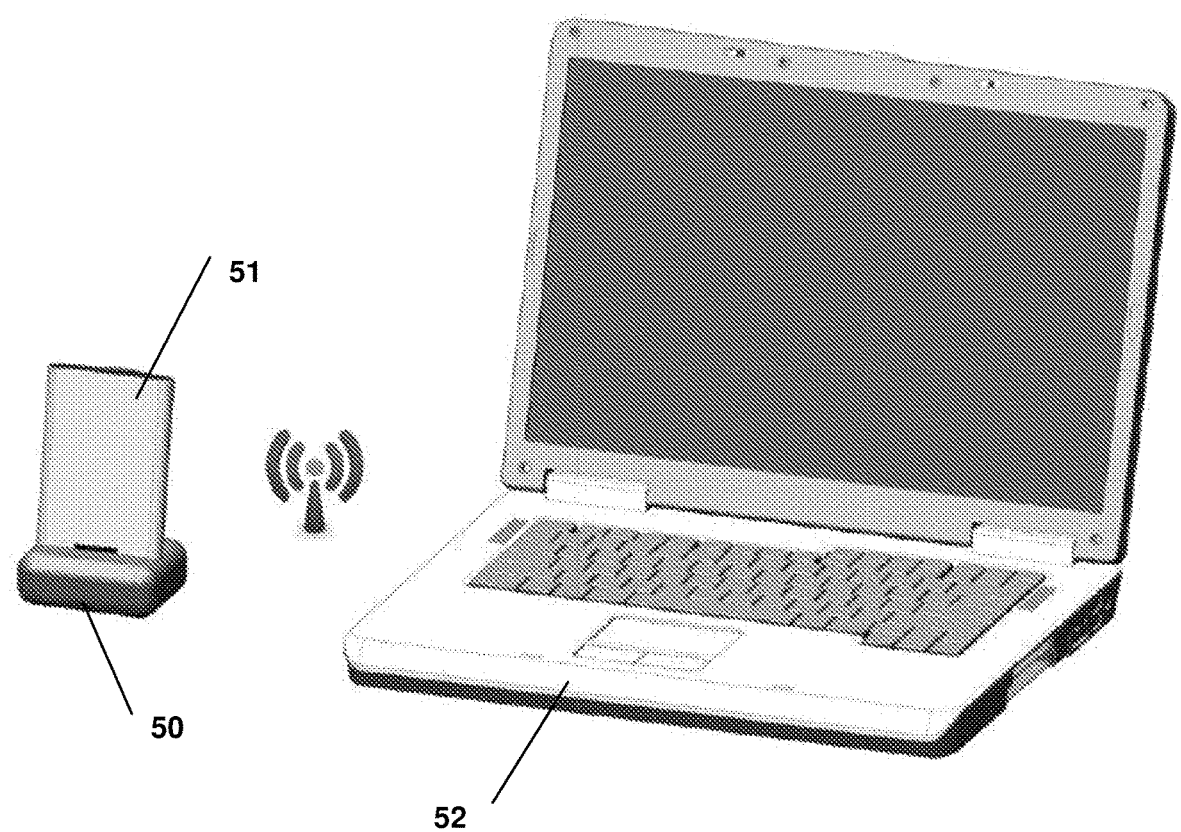
FIG. 5 shows a non-limiting example of a system for providing remote medical therapy to a subject in a healthcare encounter; in this case, a technology device connected to an apparatus for dispensing medicaments via a wireless interface.

Referring to FIG. 5, in a particular embodiment, a system for providing remote medical therapy to a subject in a healthcare encounter includes a networked laptop computer 52 running software applications to facilitate communications between a telemedical care provider and a subject or a subject's caregiver. In this embodiment, the laptop is in communication with the laptop computer 52 and an apparatus for dispensing medicaments 51 via a connector device 50 utilizing a wireless communications protocol. The connector device, in this case, provides communication between the laptop computer 52 and the apparatus for dispensing medicaments 51 such that a live, remote telemedical care provider can monitor and/or operate the dispensing apparatus. Wirelessly connected components of the system increase portability and facilitate access to subjects. In this embodiment, the device is optionally in communication with the medicament dispensing apparatus 51 and networked device 52 via a NFC protocol or a wi-fi protocol.

In many embodiments, NFC connected devices allow rapid configuration and re-configuration based on health and economic risks faced by a particular subject, family, or population. In some embodiments, the medical therapy device includes a RFID reader that may contain a barcode reader. The RFID reader included with the medical therapy device may be powered by a cable or battery and pings a RFID tag included in the apparatus for dispensing one or more medical items, which includes standard prescription labeling, including drug name, dosage, expiration date, lot number, and the like. The RFID transponder included in the apparatus for dispensing one or more medical items for transmitting information to the RFID reader included with the medical therapy device may be a passive or active transponder operating in the low frequency, high frequency, or ultra-high frequency domain. In alternative embodiments, the RFID reader is included in the apparatus for dispensing one or more medical items and the RFID tag included in the medical therapy device.

In some embodiments, one or more components of a medical therapy device are non-portable or fixed in a stationary installation. For example, in a particular embodiment, one or more biosensors are fixed in a stationary installation to increase access to subjects at a centralized location. In another particular embodiment, the telecommunications component is fixed in a stationary installation to increase access to subjects at a centralized location. In another particular embodiment, an apparatus for dispensing medical items is fixed in a stationary installation to increase access to subjects at a centralized location.

Referring to FIGS. 4 and 5, in particular embodiments, an apparatus for dispensing one or more medical items to a subject in a healthcare encounter is operated remotely by a live, licensed healthcare provider. In other embodiments, an apparatus for dispensing one or more medical items to a subject operates in an emergency mode and dispenses one or more medical items autonomously (e.g., without remote operation by a live healthcare provider). In further embodiments, an apparatus for dispensing one or more medical items operating in an emergency mode utilizes a module for risk assessment and/or diagnostic/therapeutic analysis to guide dispensing determinations. In still further embodiments, an apparatus for dispensing one or more medical items operating in an emergency mode activates the emergency response system (e.g., police, fire, EMS, etc.).

Figure 6:
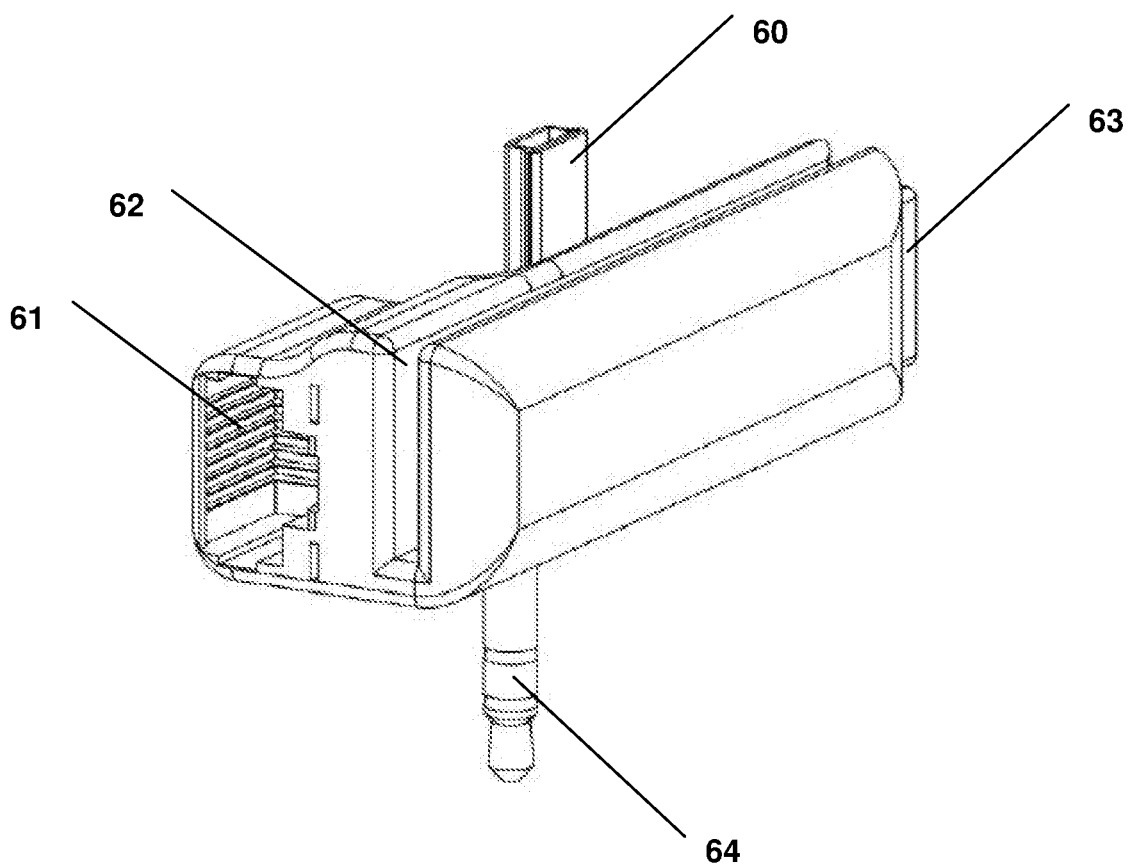
FIG. 6 shows a non-limiting example of a device for providing remote medical therapy to a subject in a healthcare encounter; in this case, a device including a magnetic stripe reader and a variety of communication interfaces.

Referring to FIG. 6, in a particular embodiment, a device for providing remote medical therapy to a subject in a healthcare encounter includes a USB mini/micro-connector 60 for connecting to an apparatus for dispensing medical items; a phone jack 61 for connecting to a land line telephone, cable box, satellite box or the like; a card reader slot 62 for reading a magnetic stripe (also called a magstripe) on a card and/or the apparatus for dispensing one or more medical items. The card reader slot 62 may be used to read a magnetic stripe from a credit card, insurance card, membership card, or the like. A USB connector (type A, type B, or mini/micro-connector) 63 allows a connection to a networked technology device. Additionally, the device includes an output jack 64 for communicating with a mobile device via a microphone port or audio jack located on a mobile device. In some embodiments, the technology device includes the necessary software for decoding the information contained within the magnetic stripe card and swiped in the card reader slot 62. In some embodiments, the card reader slot 62, reads a magnetic stripe contained on the apparatus for dispensing one or more medical items from an inventory of medical items including information such as standard prescription labeling, including drug name, dosage, expiration date, lot number, and the like. In various embodiments, one or more of the connectors (60, 63, 64) is reversibly retractable within the housing. In various embodiments, one or more of the connectors (60, 64) is swivels about an axis with respect to the housing to allow it to fold into the housing. In such embodiments with retractable or folding connectors, the device is portable and easy to store.

Other relevant information contained on the magnetic stripe on the apparatus for dispensing one or more medical items includes patient identifying information, insurance information, and/or service membership information. Membership information may include such information as identification of membership in healthcare services, pharmaceutical services including retail pharmacy memberships and the like. In some embodiments, the card reader slot forms a part of the apparatus for dispensing one or more medical items from an inventory of medical items. In one embodiment, the magnetic stripe may be located on the medical therapy device and swiped through the slot forming a part of the apparatus for dispensing one or more medical items and includes such information as standard prescription labeling, including drug name, dosage, expiration date, lot number, patient identifying information, insurance information, membership information, and the like. The magnetic stripe may be retractable within the medical therapy device or the apparatus for dispensing one or more medical items.

Figure 7:
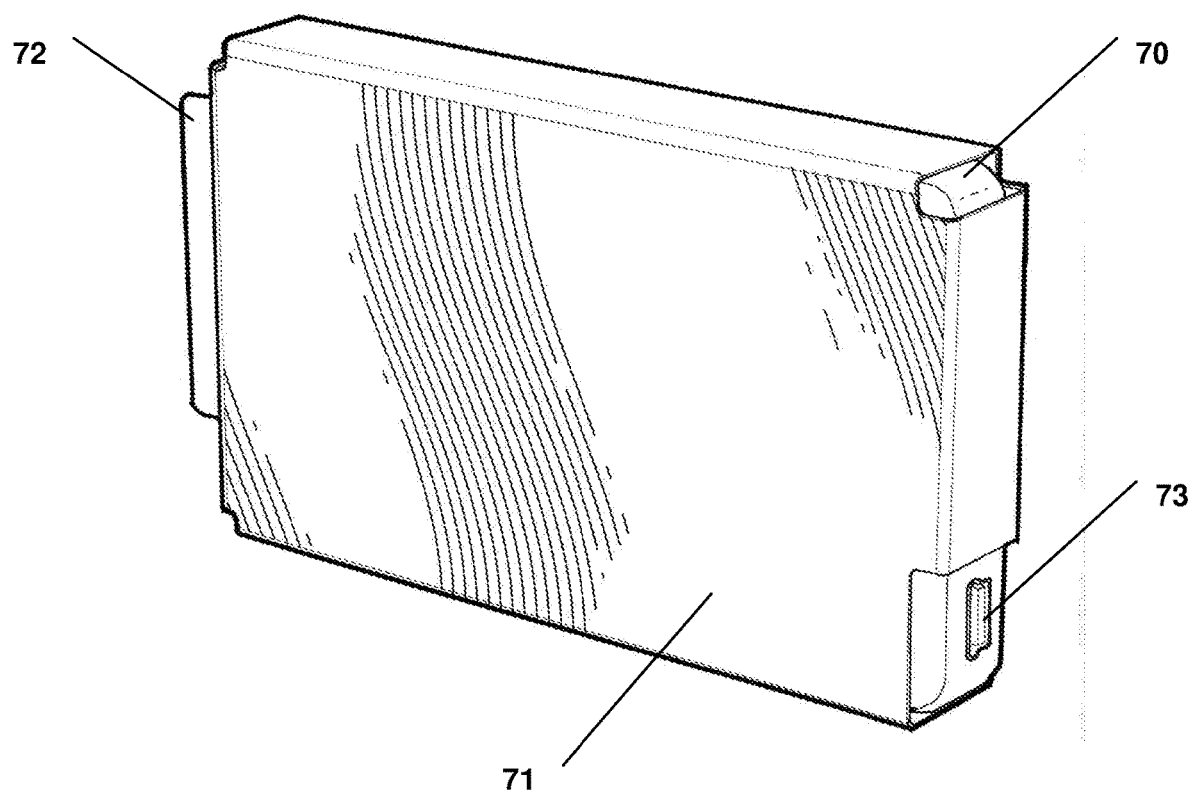
FIG. 7 shows a non-limiting, exemplary view of an apparatus for dispensing medical items; in this case, an apparatus including a communications connector, a magnetic stripe, and a protective opaque sleeve.

Referring to FIG. 7, in a particular embodiment, an apparatus for dispensing one or more medical items to a subject in a healthcare encounter 70 in encased in an opaque, protective sleeve 71 and includes a magnetic stripe 72 and a mini-USB type B connector 73. In this embodiment, the protective sleeve 71 provides one layer of child resistance by preventing opening of the apparatus and access to the medicaments therein. Further in this embodiment, the magnetic stripe 72 provides information about, for example, the medicaments to a technology device or a connector device fitted with a magnetic stripe reader. Also in this embodiment, the USB connector 73 provides communication with a technology device.

Figure 8:
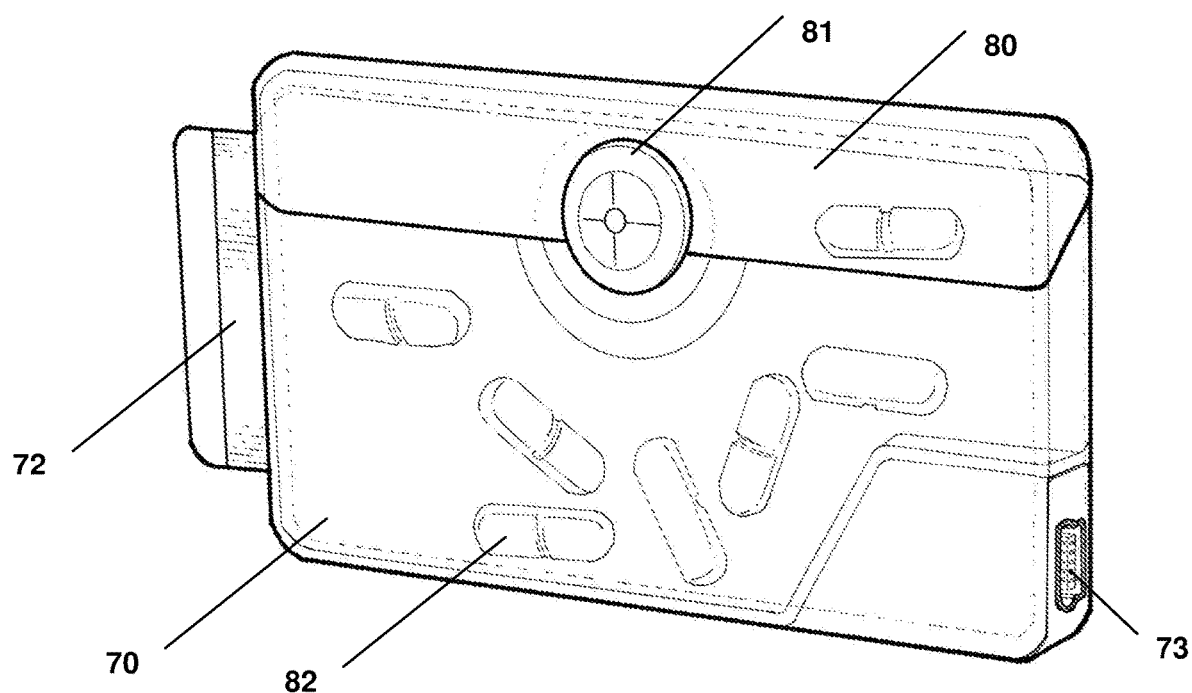
FIG. 8 shows another non-limiting, exemplary view of an apparatus for dispensing medical items; in this case, an apparatus containing multiple units of a medicament and including a lid with a closure mechanism in a closed position, a communications connector, a magnetic stripe.

Referring to FIG. 8, in a particular embodiment, an apparatus for dispensing one or more medical items to a subject in a healthcare encounter 70 is removed from the opaque, protective sleeve (not shown) and includes a magnetic stripe 72 and a mini-USB type B connector 73. In this embodiment, the apparatus includes a mechanism 81 that allows opening and closing of a hinged lid 80 and access to the medicaments 82 therein. In this embodiment, the lid opening/closing mechanism 81 provides another layer of child resistance by preventing opening of the apparatus and access to the medicaments therein.

Figure 9:
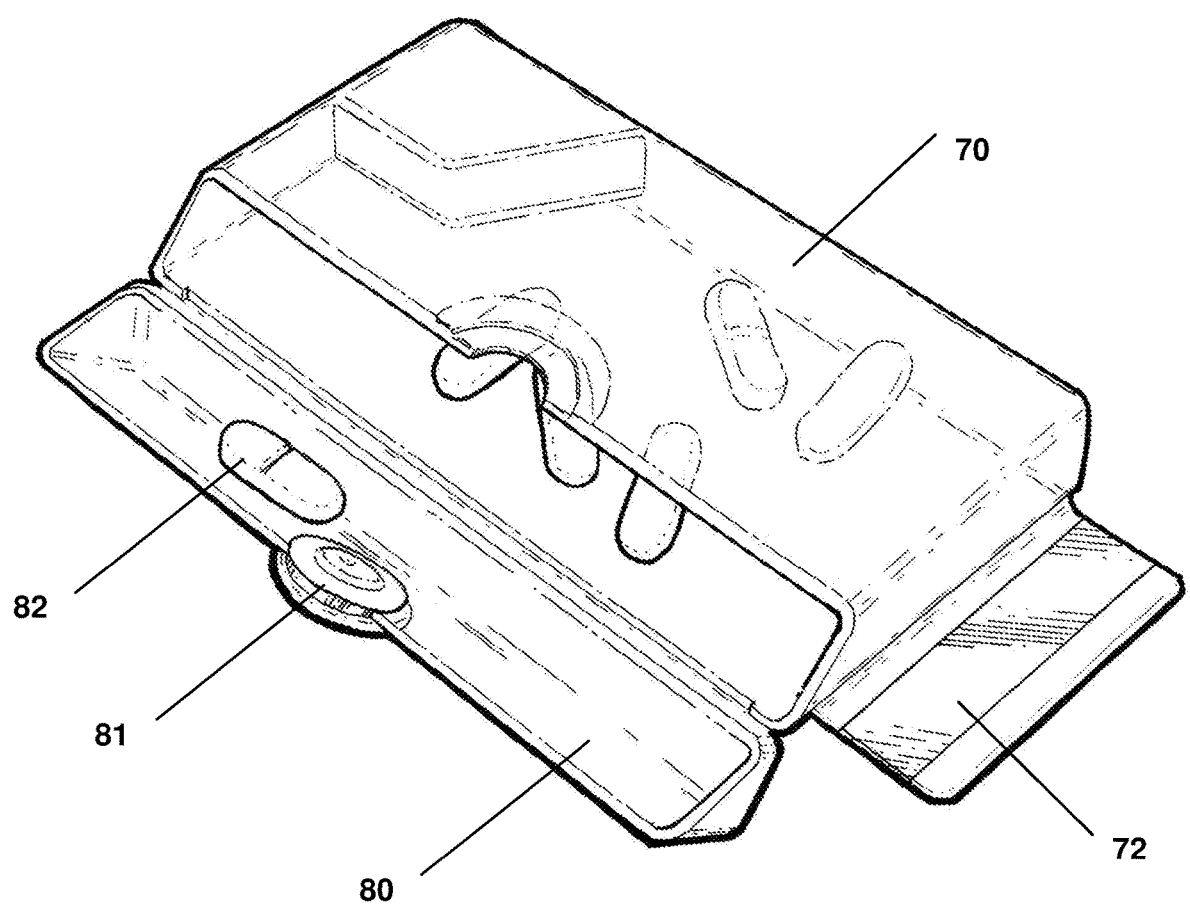
FIG. 9 shows another non-limiting, exemplary view of an apparatus for dispensing medical items; in this case, an apparatus containing multiple units of a medicament and including a lid with a closure mechanism in an open position, a communications connector, a magnetic stripe.

Referring to FIG. 9, in a particular embodiment, an apparatus for dispensing one or more medical items to a subject in a healthcare encounter 70 is removed from the opaque, protective sleeve (not shown) and includes a magnetic stripe 72. In this embodiment, the apparatus includes a mechanism 81 that has been released and the hinged lid 80 opened to allow access to the medicaments 82 therein.

Figure 10:
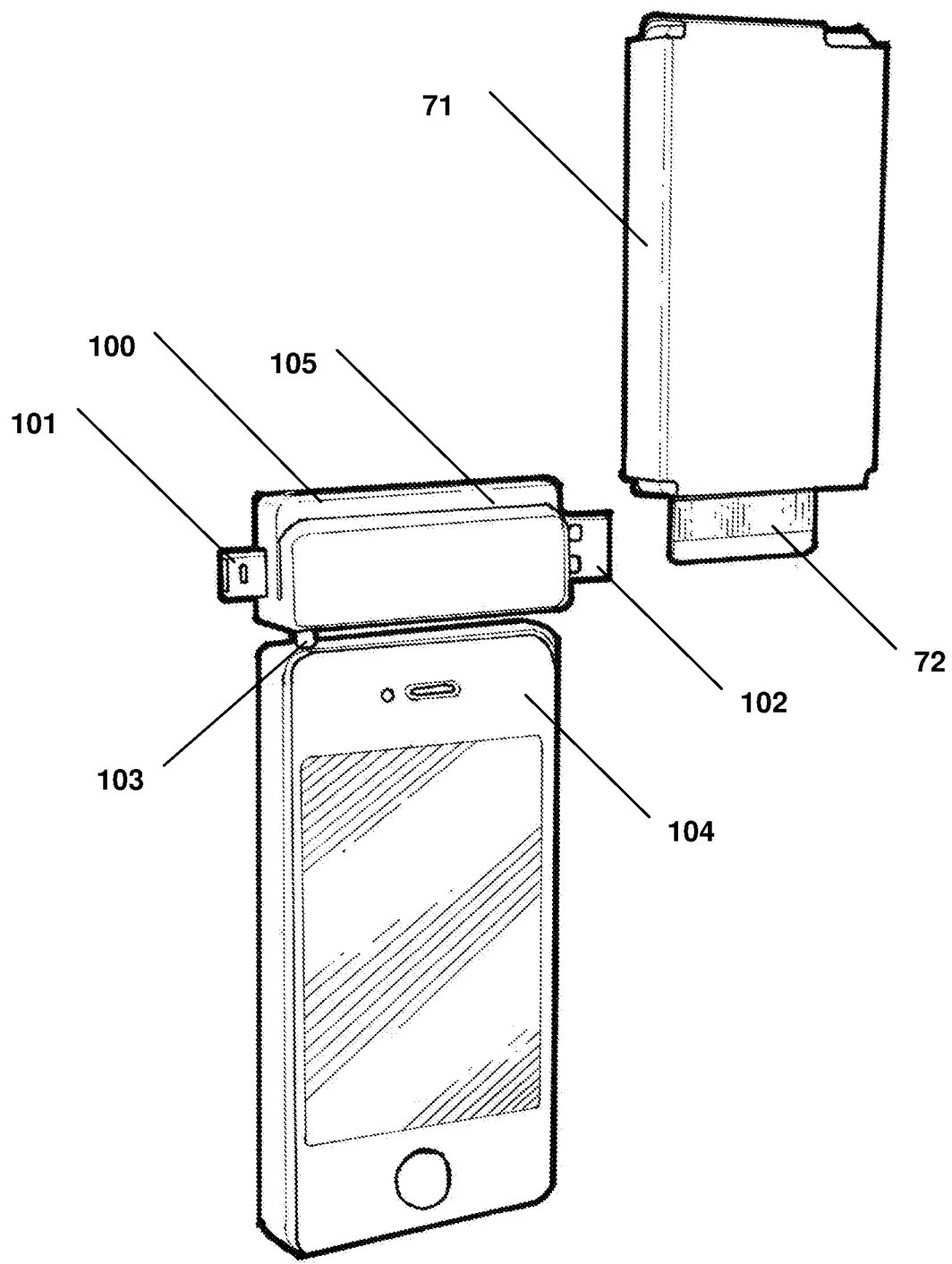
FIG. 10 shows a non-limiting example of a system for providing remote medical therapy to a subject in a healthcare encounter; in this case, a system including technology device, a connector device with a magnetic stripe reader, and an apparatus for dispensing medical items.

Referring to FIG. 10, in a particular embodiment, a system for dispensing one or more medical items to a subject in a healthcare encounter includes a technology device 104, in this case a mobile smartphone. The system also includes a connector device 100 with three different connectors: 1) a mini-USB connector 101, 2) a USB type A connector 102, and 3) an audio jack connector 103. In this embodiment, the smartphone is in communication with the connector device by coupling via the audio jack. The connector device further includes a magnetic card reader 105 for reading information from a variety of sources including, for example, a subject ID card, a financial transaction card, a medical insurance card, and an apparatus for dispensing medical items to a subject. The system also includes an apparatus for dispensing one or more medical items to a subject in a healthcare encounter. In this case, the apparatus is in a protective sleeve 71 and includes a magnetic stripe 72 for identifying, for example, the medical items contained in the apparatus. In this embodiment, when the apparatus is swiped through the magnetic stripe reader 105 of the connector device 100 the technology device 104 is utilized to allow verification that the medical item is appropriate for the subject. Remote verification that the medical item is appropriate for the subject in the healthcare encounter provides yet another layer of child resistance and accident/abuse prevention.

In some embodiments, confirmation of an appropriate apparatus for dispensing medical items for the subject in the healthcare encounter is provided via one or more confirmation components of the connector device. In some embodiments, the networked technology device is further configured to allow identification of the subject, collection of biosensor data, performance of audio/video conferencing between the subject and one or more live, remote telemedical care providers. In further embodiments, a lid opening/closing mechanism is remotely monitored and/or operated by a live, remote telemedical care provider.

Figure 11:
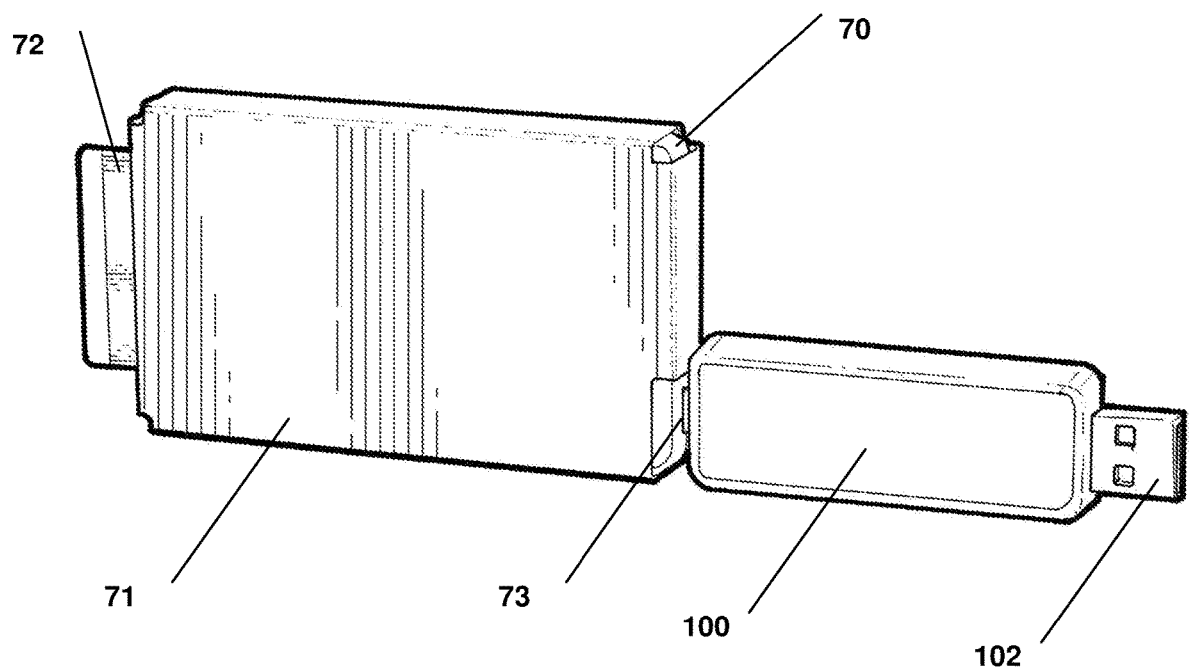
FIG. 11 shows a non-limiting example of a system for providing remote medical therapy to a subject in a healthcare encounter; in this case, a system including a connector device with a USB interface and an apparatus for dispensing medical items.

Referring to FIG. 11, in a particular embodiment, a system for dispensing one or more medical items to a subject in a healthcare encounter includes a connector device 100 with two different connectors: 1) a mini-USB connector and 2) a USB type A connector 102. The system also includes an apparatus for dispensing one or more medical items to a subject in a healthcare encounter 70. In this case, the apparatus is in a protective sleeve 71 and includes a mini- USB connector 73 and a magnetic stripe 72 for identifying, for example, the medical items contained in the apparatus. In this embodiment, the apparatus 70 is in communication with the connector device 100 by coupling via the mini-USB connector 73. In this embodiment, the connector device is further available for connection to a networked technology device via a free USB connector 102.

The devices and systems disclosed herein offer multiple layers of childproofing and child resistance. In various embodiments, the childproofing mechanisms include, by way of non-limiting examples, an opaque protective sleeve that conceals the medical items within the dispensing apparatus, a protective child-resistant wrapper over the apparatus, a tamper-proof opening/closing mechanism for the dispensing apparatus, and electronic verification that the medical items within the dispensing apparatus are appropriate for a particular subject in a healthcare encounter.

Figure 12:
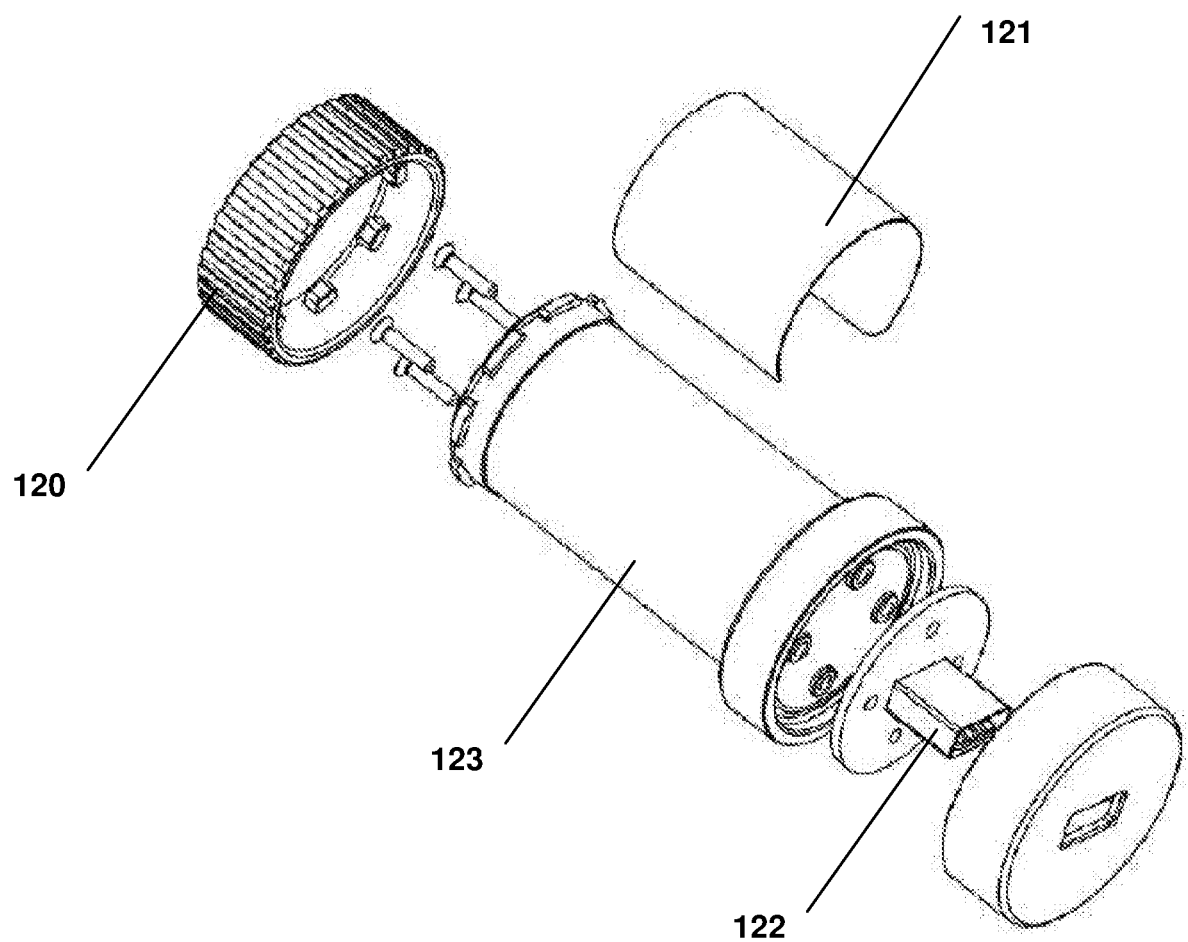
FIG. 12 shows a non-limiting example of a system for providing remote medical therapy to a subject in a healthcare encounter; in this case, an apparatus for dispensing medicaments integrated with a connector device for providing communication with a technology device.

Referring to FIG. 12, in a particular embodiment, an apparatus for dispensing one or more medical items to a subject is a disposable device designed for individual use. In this embodiment, an apparatus for dispensing one or more medical items includes a locking cap 120, unlocked remotely by a healthcare provider (e.g., pharmacist, nurse, physician, etc.). The locking mechanism is any form of locking mechanism known to those of ordinary skill in the art wherein the locking mechanism is controlled remotely. Further in this embodiment, the apparatus includes standard prescription labeling 121, including drug name, dosage, expiration date, lot number, and the like. To facilitate communication via USB with the device disclosed herein, the apparatus includes a USB interface 122, of a standard USB connector Type A or B or Mini/Micro-connector. The prescribed medicaments are housed individually or in unit dose packaging in a suitable container 123 and of a suitable size based on the particular type of prescribed medicament and amount and duration of therapy prescribed.

Non-Transitory Computer Readable Storage Medium

In some embodiments, the devices, systems, software, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the devices, systems, software, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Software Modules

In some embodiments, the devices, systems, software, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the devices, systems, software, and methods disclosed herein include one or more databases, or use of the same. In view of the disclosure provided herein, those of skill in the art will recognize that many databases are suitable for storage and retrieval of subject, medication, provider, and/or insurance information. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

EXAMPLE

The following illustrative example is representative of an embodiment of the devices, systems, software, and methods described herein and are not meant to be limiting in any way.

Live, Remote, Adjunct Triage

A 25-year-old female subject, living in Texas, is experiencing symptoms associated with X. The nearest medical facility is at least a few hundred miles away. Previously, the female was seen by her primary care physician who identified, based on a risk profile analysis, the statistical likelihood of the patient experiencing symptoms associated with X in the near future. Upon the occurrence of the symptoms, the female, using a networked device, connects to a live, remote, adjunct provider. The provider, a physician assistant (PA) located in California, is credentialed by the researcher's healthcare provider who verified the PA's education, training, certifications, references, prescription license, malpractice insurance coverage, and state license and state of licensure. The PA asks basic questions about the subject's symptoms and examines the subject visually. To gather additional information, the PA instructs the subject to use the biometric sensor equipped in her networked device. The biometric sensor measures the subject's vital signs and other biometric data such as her body temperature, heart rate, blood pressure, and respiratory rate. The PA obtains the subject's consent to access her electronic health records. Using a software program, which is updated regularly to meet applicable legal requirements, the PA accesses the subject's medical history, medication history, family history, and other relevant information. Based on the information gathered by the PA, the subject is instructed to connect her medical therapy device and the apparatus for dispensing the pre-prescribed medicaments for X to the networked device. The apparatus is confirmed visually as containing the pre-prescribed medications for X and remotely unlocked by the PA.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

We claim:

1. A system for providing a healthcare treatment to a subject comprising:
an apparatus adapted to dispensing one or more medical items comprising: a container for storing the one or more medical items therein; a lid or a cap or a portion of the container for enclosing and providing access to the one or more medical items inside the container; and a communications device adapted to providing a remote or an autonomous opening of the lid, the cap, or the portion of the container; and
a connector device comprising: a first communications device for connecting with the communications device of the dispensing apparatus; a second communications device for connecting with a technology device; and a processor-executable software module adapted to communicating with the dispensing apparatus using the first communications device and communicating with the technology device using the second communications device,
wherein the one or more medical items enclosed in the container are selected in advance of a need for the one or more medical items, from an inventory of medical items risk profiled based on a probability calculation of a health or a risk assessment of the subject, a population including the subject, or an event, and
wherein when the connector device connects the dispensing apparatus to the technology device, the lid, the cap, or the portion of the container enclosing the one or more medical items is openable by a remote telemedicine care provider or autonomously without a telemedicine care provider thereby providing access by the subject to the one or more medical items.

2. The system of claim 1, wherein the communications device of the dispensing apparatus is a USB connector or a magnetic stripe, and wherein the first communications device of the connector device is a corresponding USB socket or a magnetic stripe reader.

3. The system of claim 1, wherein the one or more medical items include one or more individual medical item stored loosely in the container or in one or more unit dose packages.

4. The system of claim 1, wherein the connector device further comprises a confirmation component, the confirmation component indicating, responsive to a remote verification by the remote telemedicine care provider, if the correct dispensing apparatus for dispensing the one or more medical items is in communication with the technology device, and wherein the confirmation component provides a visual confirmation, an audible confirmation, a tactile confirmation, or a combination thereof.

5. The system of claim 1, wherein the technology device further comprises a payment information stored therein sufficient for completing a purchase of the one or more medical items, and wherein when the dispensing apparatus, the connector device, and the technology device are connected together, the lid or the cap or the portion of the container enclosing the one or more medical items may be enabled for opening after the subject is in need of the one or more medical items and the payment information is communicated by the technology device to purchase the one or more medical items.

6. The system of claim 1, wherein the technology device further comprises a barcode reader, a magnetic stripe reader, or a radiofrequency identification (RFID) token interrogator, wherein the barcode reader and the magnetic stripe reader are configured to read a barcode or a magnetic stripe, respectively.

7. The system of claim 6, wherein the dispensing apparatus further comprises the barcode, the magnetic stripe, or an RFID token positioned thereon.

8. The system of claim 1, further comprising a label having an information portion including information providing an identification of the one or more medical items stored in the container.

9. The system of claim 1, wherein the technology device is further configured to couple wirelessly with the dispensing apparatus.

10. The system of claim 1, wherein the remote telemedicine care provider is selected from the group consisting of a physician, a pharmacist, a dentist, a physician assistant, a nurse practitioner, a registered nurse, a pharmacist, a chiropractor, an emergency medical technician, a licensed practical nurse, a certified ultrasound technician, a psychologist, a social worker, a military medic, a physical therapist, an occupational therapist, a speech therapist, a radiology technician, a cardiac catheterization technician, a clinical pathology laboratory technician, a medical aesthetician, a licensed medical technologist, a toxicologist consultant, a credentialed medical legal consultant, a credentialed hospital operations administrator, veterinarian or a veterinary nurse, assistant, or technician.

11. The system of claim 1, wherein the connector device or the technology device are further configured to receive information useful in confirming an identity of the subject.

12. The system of claim 1, further comprising a biosensor device configured to transmit biometric data about the subject or medical information from the subject to the remote telemedicine care provider for use in remote diagnosis or therapy including determining when or if the subject will be in need of or is in need of the one or more medical items, the need being based on a probabilistic assessment of the subject using the biometric data or the medical information.

13. The system of claim 1, further comprising an input device adapted to receiving data from the subject for use in determining when or if the subject will be in need of or is in need of the one or more medical items, wherein the input device selected from one or more of the group consisting of a keyboard, a keypad, a touch screen, a multi-touch screen, a pointing device, a microphone, or a video camera.

14. The system of claim 1, wherein the technology device is a computer, a mobile device, a hard wired telephone, a set top box, an internet appliance, or a medical diagnostic device.

* * * * *